United States Patent
Almeida et al.

(10) Patent No.: US 9,890,372 B2
(45) Date of Patent: Feb. 13, 2018

(54) ASPARTIC PROTEASES

(71) Applicant: BIOCANT—ASSOCIAÇÃO DE TRANSFERÊNCIA DE TECNOLOGIA, Cantanhede (PT)

(72) Inventors: Carla Sofia Gomes Malaquias de Almeida, Cantanhede (PT); Isaura Isabel Gonçalves Simões, Cantanhede (PT); Carlos José Fialho Costa Faro, Cantanhede (PT)

(73) Assignee: BIOCANT—ASSOCIAÇÃO DE TRANSFERÊNCIA DE TECNOLOGIA, Cantanhede (PT)

( * ) Notice: Subject to any disclaimer, the term of this patent is extended or adjusted under 35 U.S.C. 154(b) by 0 days.

(21) Appl. No.: 14/777,848

(22) PCT Filed: Mar. 19, 2014

(86) PCT No.: PCT/PT2014/000018
§ 371 (c)(1),
(2) Date: Sep. 17, 2015

(87) PCT Pub. No.: WO2014/148932
PCT Pub. Date: Sep. 25, 2014

(65) Prior Publication Data
US 2016/0186160 A1    Jun. 30, 2016

(30) Foreign Application Priority Data

Mar. 19, 2013 (GB) .................................. 1305023.2

(51) Int. Cl.
*C12N 9/50* (2006.01)
*A61K 38/00* (2006.01)
*A61K 48/00* (2006.01)

(52) U.S. Cl.
CPC .............. *C12N 9/63* (2013.01); *C12Y 304/23* (2013.01); *A61K 38/00* (2013.01); *A61K 48/005* (2013.01)

(58) Field of Classification Search
CPC .......... C12N 9/63; C12N 9/50; C12Y 304/23; A23C 19/041; A23C 9/1209; A61K 38/00; A61K 48/005; A61K 36/28; A61K 38/488
See application file for complete search history.

(56) References Cited

U.S. PATENT DOCUMENTS

| | | | |
|---|---|---|---|
| 2002/0102285 A1 | 8/2002 | Bishop et al. | |
| 2006/0003435 A1* | 1/2006 | Soares Pais | C12N 9/50 435/254.2 |
| 2006/0240053 A1 | 10/2006 | Bernard et al. | |
| 2011/0104286 A1* | 5/2011 | Soares Pais | A61K 36/28 424/489 |
| 2011/0177052 A1 | 7/2011 | Chavan | |
| 2016/0083711 A1 | 3/2016 | de Almeida et al. | |

FOREIGN PATENT DOCUMENTS

| | | |
|---|---|---|
| CN | 103027882 A | 4/2013 |
| EP | 2508616 A1 | 10/2012 |
| HU | 57608 A2 | 12/1991 |
| JP | 10-139652 | 5/1998 |
| JP | 2003-40769 A | 2/2003 |
| WO | WO95/07687 | 3/1995 |
| WO | WO 2009/040778 A1 | 4/2009 |
| WO | WO 2014/148931 A2 | 9/2014 |

OTHER PUBLICATIONS

Bi et al. Plant Cell Physiol. 46(1): 87-98 (2005), "The Rice Nucellin Gene Ortholog OsAsp1 Encodes an Active Aspartic Protease Without a Plant-specific Insert and is Strongly Expressed in Eerly Embryo".
Bryksa et al. The Journal of Biological Chemistry vol. 286, No. 32, pp. 28265-28275, Aug. 12, 2011 "Structure and Mechanism of the Saposin-like Domain of a Plant Aspartic Protease".
Cordeiro et al. Milchwissenschaft 47 (11) 1992, "Milk clotting and proteolytic activities of purified cynarases from Cynara cardunculus—a comparison to chymosin".
Curto Pedro et al. Applied and Environmental Microbiology, American Society for Microbiology, US, vol. 80, No. 1, Jan. 2014, pp. 86-96, "Establishing the yeast *Kluyveromyces lactis* as an expression host for production of the saposin-like domain of the aspartic protease cirsin".
Egas et al. The Journal of Biological Chemistry. vol. 275, No. 49, Issue of Dec. 8, 2000 pp. 38190-38196, "The Saposin-like Domain of the Plant Aspartic Proteinase Precursor Is a Potent Inducer of Vesicle Leakage".
Horikoshi et al. British Journal of Dermatology, vol. 141, No. 3, Sep. 24, 1999, pp. 453-459, "Role of endogenous cathepsin D-like and chymotrypsin-like proteolysis in human epidermal desquamation".
International Search Report and Written Opinion issued in PCT/PT2014/000018 dated Nov. 6, 2014.
International Search Report and Written Opinion issued in PCT/PT2014/000017 dated Nov. 6, 2014.
Lufrano et al. FEBS Journal 279 (Suppl. 1) (2012) 52-576, "Analysis of the expression of plant specific insert (PSI) domain in the nonconventional system Kluveromyces lactis".
Mazorra-Manzano M A et al. Phytochemistry, Pergamon Press, GB, vol. 69, No. 13, Oct. 2008, pp. 2439-2448, "Expression and characterization of the recombinant aspartic proteinase A1 from *Arabidopsis thaliana*".

(Continued)

*Primary Examiner* — Debbie K Ware
(74) *Attorney, Agent, or Firm* — Swanson & Bratschun, L.L.C.

(57) ABSTRACT

Methods and composition, thereof, relate to aspartic proteases, and particularly to aspartic proteases for plants. Disclosed are modified plant aspartic proteases, and methods for their manufacture, and uses thereof. Particularly contemplated are the uses of aspartic proteases in inducing skin desquamation.

11 Claims, 8 Drawing Sheets

(56) References Cited

OTHER PUBLICATIONS

Milisavljevic M DJ et al. Journal of Plant Physiology, Urban Und Fischer Verlag, DE vol. 165, No. 9, Jun. 16, 2008, pp. 983-990, "Two types of aspartic proteinases from buckwheat seed—Gene structure and expression analysis".
Munoz et al. Peptides 21 (2010) 777-785, "The swaposin-like domain of potato aspartic protease (StAsp-PSI) exerts antimicrobial activity on plant and human pathogens".
Payie et al. Biochem, J. (2003) 372, 671-678, "Construction, expression and characterization of a chimaeric mammalian—plant-aspartic proteinase".
Picon et al. Milchwissenschaft 50 (7) 1995 393-395, "Kinetics of milk coagulation by mixtures of cyprosin and chymosin".
Prasad et al. Protein Expression and Purification Academic Press, San Diego, CA, vol. 72, No. 2, Aug. 2010, pp. 169-174, "Heterologous expression and characterization of recombinant OsCDR1, a rice aspartic proteinase involved in disease resistance".
Ramalho-Santos et al. Eur. J. Biochem. 255, 133-138 (1998), "Identification and proteolytic processing of procardosin A".
Sampaio et al. Journal of Bioscience and Bioengineering, Elsevier, Amsterdam, NL, vol. 105, No. 4, Apr. 2008 pp. 305-312, "Production and characterization of recombinant cyposin B in *Saccharomyces cerevisiae* (W303-1A) strain".
Törmäkängas et al. The Plant Cell, vol. 13(9), 2021-2032, Sep. 2001, "A Vacuolar Sorting Domain May Also Influence the Way in Which Proteins Leave the Endoplasmic Reticulum".
White et al. Journal of Biological Chemistry, American Society for Biochemistry and Molecular Biology, US, vol. 274, No. 24, Jun. 11, 1999, pp. 16685-16693, "Processing, activity, and inhibition of recombinant cyprosin, an aspartic proteinase from Cardoon (*Cynara cardunculus*)".

\* cited by examiner pCBwoPSI (proCardosin B sequence without the PSI sequence):
MVSNGGLLRVGLKKRKVDRLDQLRAHGVHMLGNARKDFGFRRTLRDSGSGIVALT
NDRDTAYYGEIGIGTPPQNFAVIFDTGSSDLWVPSTKCDTSLACVIHPRYDSGDSST
YKGNGTTASIQYGTGAIVGFYSQDSVEVGDLVVEHQDFIETTEEDDTVFLKSEFDGI
LGLGFQEISAGKAVPVWYNMVNQGLVEEAVFSFWLNRNVDEEEGGELVFGGVDP
NHFRGNHTYVPVTRKGYWQFEMGDVLIGDKSSGFCAGGCAAIADSGTSFFAGPTAI
ITQINQAIGAKGGGGSAESIVDCNGISSMPNIAFTIGSKLFEVTPEQYIYKVGEGEAAT
CISGFTALDIMSPQGPIWILGDMFMGPYHTVFDYGKLRVGFAEAV
[SEQ ID NO: 1]

pCAwoPSI (proCardosin A sequence without the PSI sequence):
MSDDGLIRIGLKKRKVDRIDQLRGRRALMEGNARKDFGFRGTVRDSGSAVVALTND
RDTSYFGEIGIGTPPQKFTVIFDTGSSVLWVPSSKCINSKACRAHSMYESSDSSTYK
ENGTSGAIIYGTGSITGFFSQDSVTIGDLVVKEQDFIEATDEADNVFLHRLFDGILGLS
FQTISVPVWYNMVNQGLVKERRFSFWLNRNVDEEEGGELVFGGLDPNHFRGDHT
YVPVTYQYYWQFGIGDVLIGDKSTGFCAPGCQAFADSGTSLLSGPTAIVTQINHAIG
ANGGGGSEELQVDCNTLSSMPNVSFTIGGKKFGLTPEQYILKVGKGEATQCISGFT
AMDATLLGPLWILGDVFMRPYHTVFDYGNLLVGFAEAA
[SEQ ID NO: 2]

pCA PSI sequence:
VMNQQCKTVVSRYGRDIIEMLRSKIQPDKICSHMKLCTFDGARDVSSIIESVVDKNN
DKSSGGIHDEMCTFCEMAVVWMQNEIKQSETEDNIINYANELCEHLSTS
[SEQ ID NO: 3]

pCB PSI sequence:
VLNQQCKTLVGQYGKNMVQMLTSEVQPDKICSHMKLCTFDGAHDVRSMIESVVDK
NNDKSSGGEICTFCEMALVRMQNEIKRNETEDNIINHVNEVCDQLPTS
[SEQ ID NO: 4]

pCB (proCardosin B sequence):
MVSNGGLLRVGLKKRKVDRLDQLRAHGVHMLGNARKDFGFRRTLRDSGSGIVALT
NDRDTAYYGEIGIGTPPQNFAVIFDTGSSDLWVPSTKCDTSLACVIHPRYDSGDSST
YKGNGTTASIQYGTGAIVGFYSQDSVEVGDLVVEHQDFIETTEEDDTVFLKSEFDGI
LGLGFQEISAGKAVPVWYNMVNQGLVEEAVFSFWLNRNVDEEEGGELVFGGVDP
NHFRGNHTYVPVTRKGYWQFEMGDVLIGDKSSGFCAGGCAAIADSGTSFFAGPTAI
ITQINQAIGAKGVLNQQCKTLVGQYGKNMVQMLTSEVQPDKICSHMKLCTFDGAHD
VRSMIESVVDKNNDKSSGGEICTFCEMALVRMQNEIKRNETEDNIINHVNEVCDQLP
TSSAESMVDCNGISSMPNIAFTIGSKLFEVTPEQYIYKVGEGEAATCISGFTALDIMS
PQGPIWILGDMFMGPYHTVFDYGKLRVGFAEAV
[SEQ ID NO: 5]

Figure 7 pCA (proCardosin A sequence):
MSDDGLIRIGLKKRKVDRIDQLRGRRALMEGNARKDFGFRGTVRDSGSAVVALTND
RDTSYFGEIGIGTPPQKFTVIFDTGSSVLWVPSSKCINSKACRAHSMYESSDSSTYK
ENGTSGAIIYGTGSITGFFSQDSVTIGDLVVKEQDFIEATDEADNVFLHRLFDGILGLS
FQTISVPVWYNMVNQGLVKERRFSFWLNRNVDEEEGGELVFGGLDPNHFRGDHT
YVPVTYQYYWQFGIGDVLIGDKSTGFCAPGCQAFADSGTSLLSGPTAIVTQINHAIG
ANGVMNQQCKTVVSRYGRDIIEMLRSKIQPDKICSHMKLCTFDGARDVSSIIESVVD
KNNDKSSGGIHDEMCTFCEMAVVWMQNEIKQSETEDNIINYANELCEHLSTSSEEL
QVDCNTLSSMPNVSFTIGGKKFGLTPEQYILKVGKGEATQCISGFTAMDATLLGPLW
ILGDVFMRPYHTVFDYGNLLVGFAEAA
    [SEQ ID NO: 6]

pCB-XhoI
CTCGAGAAAAGAATGGTCTCCAACGGCGGATTGCTTC
    [SEQ ID NO:7]

pCB-SalI
GTCGACTCAAACTGCTTCTGCAAATCCCACTCGTAAC
    [SEQ ID NO:8]

Figure 7 (cont'd)

SEQUENCE LISTING

```
<160> NUMBER OF SEQ ID NOS: 12

<210> SEQ ID NO 1
<211> LENGTH: 383
<212> TYPE: PRT
<213> ORGANISM: Artificial sequence
<220> FEATURE:
<223> OTHER INFORMATION: Synthetic construct

<400> SEQUENCE: 1

Met Val Ser Asn Gly Gly Leu Leu Arg Val Gly Leu Lys Lys Arg Lys
1               5                   10                  15

Val Asp Arg Leu Asp Gln Leu Arg Ala His Gly Val His Met Leu Gly
            20                  25                  30

Asn Ala Arg Lys Asp Phe Gly Phe Arg Arg Thr Leu Arg Asp Ser Gly
        35                  40                  45

Ser Gly Ile Val Ala Leu Thr Asn Asp Arg Asp Thr Ala Tyr Tyr Gly
    50                  55                  60
```

Glu Ile Gly Ile Gly Thr Pro Pro Gln Asn Phe Ala Val Ile Phe Asp
65                  70                  75                  80

Thr Gly Ser Ser Asp Leu Trp Val Pro Ser Thr Lys Cys Asp Thr Ser
            85                  90                  95

Leu Ala Cys Val Ile His Pro Arg Tyr Asp Ser Gly Asp Ser Ser Thr
        100                 105                 110

Tyr Lys Gly Asn Gly Thr Thr Ala Ser Ile Gln Tyr Gly Thr Gly Ala
    115                 120                 125

Ile Val Gly Phe Tyr Ser Gln Asp Ser Val Glu Val Gly Asp Leu Val
130                 135                 140

Val Glu His Gln Asp Phe Ile Glu Thr Thr Glu Glu Asp Asp Thr Val
145                 150                 155                 160

Phe Leu Lys Ser Glu Phe Asp Gly Ile Leu Gly Leu Gly Phe Gln Glu
                165                 170                 175

Ile Ser Ala Gly Lys Ala Val Pro Val Trp Tyr Asn Met Val Asn Gln
            180                 185                 190

Gly Leu Val Glu Glu Ala Val Phe Ser Phe Trp Leu Asn Arg Asn Val
        195                 200                 205

Asp Glu Glu Glu Gly Gly Glu Leu Val Phe Gly Val Asp Pro Asn
210                 215                 220

His Phe Arg Gly Asn His Thr Tyr Val Pro Val Thr Arg Lys Gly Tyr
225                 230                 235                 240

Trp Gln Phe Glu Met Gly Asp Val Leu Ile Gly Asp Lys Ser Ser Gly
                245                 250                 255

Phe Cys Ala Gly Gly Cys Ala Ala Ile Ala Asp Ser Gly Thr Ser Phe
            260                 265                 270

Phe Ala Gly Pro Thr Ala Ile Ile Thr Gln Ile Asn Gln Ala Ile Gly
        275                 280                 285

Ala Lys Gly Gly Gly Ser Ala Glu Ser Ile Val Asp Cys Asn Gly
290                 295                 300

Ile Ser Ser Met Pro Asn Ile Ala Phe Thr Ile Gly Ser Lys Leu Phe
305                 310                 315                 320

Glu Val Thr Pro Glu Gln Tyr Ile Tyr Lys Val Gly Glu Gly Glu Ala
                325                 330                 335

Ala Thr Cys Ile Ser Gly Phe Thr Ala Leu Asp Ile Met Ser Pro Gln
            340                 345                 350

Gly Pro Ile Trp Ile Leu Gly Asp Met Phe Met Gly Pro Tyr His Thr
        355                 360                 365

Val Phe Asp Tyr Gly Lys Leu Arg Val Gly Phe Ala Glu Ala Val
370                 375                 380

<210> SEQ ID NO 2
<211> LENGTH: 377
<212> TYPE: PRT
<213> ORGANISM: Artificial sequence
<220> FEATURE:
<223> OTHER INFORMATION: Synthetic construct

<400> SEQUENCE: 2

Met Ser Asp Asp Gly Leu Ile Arg Ile Gly Leu Lys Lys Arg Lys Val
1               5                   10                  15

Asp Arg Ile Asp Gln Leu Arg Gly Arg Arg Ala Leu Met Glu Gly Asn
            20                  25                  30

Ala Arg Lys Asp Phe Gly Phe Arg Gly Thr Val Arg Asp Ser Gly Ser
        35                  40                  45

```
Ala Val Val Ala Leu Thr Asn Asp Arg Asp Thr Ser Tyr Phe Gly Glu
 50                  55                  60
Ile Gly Ile Gly Thr Pro Pro Gln Lys Phe Thr Val Ile Phe Asp Thr
 65                  70                  75                  80
Gly Ser Ser Val Leu Trp Val Pro Ser Lys Cys Ile Asn Ser Lys
                 85                  90                  95
Ala Cys Arg Ala His Ser Met Tyr Glu Ser Ser Asp Ser Ser Thr Tyr
            100                 105                 110
Lys Glu Asn Gly Thr Ser Gly Ala Ile Ile Tyr Gly Thr Gly Ser Ile
            115                 120                 125
Thr Gly Phe Phe Ser Gln Asp Ser Val Thr Ile Gly Asp Leu Val Val
130                 135                 140
Lys Glu Gln Asp Phe Ile Glu Ala Thr Asp Glu Ala Asp Asn Val Phe
145                 150                 155                 160
Leu His Arg Leu Phe Asp Gly Ile Leu Gly Leu Ser Phe Gln Thr Ile
                165                 170                 175
Ser Val Pro Val Trp Tyr Asn Met Val Asn Gln Gly Leu Val Lys Glu
                180                 185                 190
Arg Arg Phe Ser Phe Trp Leu Asn Arg Asn Val Asp Glu Glu Glu Gly
            195                 200                 205
Gly Glu Leu Val Phe Gly Gly Leu Asp Pro Asn His Phe Arg Gly Asp
210                 215                 220
His Thr Tyr Val Pro Val Thr Tyr Gln Tyr Tyr Trp Gln Phe Gly Ile
225                 230                 235                 240
Gly Asp Val Leu Ile Gly Asp Lys Ser Thr Gly Phe Cys Ala Pro Gly
                245                 250                 255
Cys Gln Ala Phe Ala Asp Ser Gly Thr Ser Leu Leu Ser Gly Pro Thr
            260                 265                 270
Ala Ile Val Thr Gln Ile Asn His Ala Ile Gly Ala Asn Gly Gly Gly
                275                 280                 285
Gly Ser Glu Glu Leu Gln Val Asp Cys Asn Thr Leu Ser Ser Met Pro
290                 295                 300
Asn Val Ser Phe Thr Ile Gly Gly Lys Lys Phe Gly Leu Thr Pro Glu
305                 310                 315                 320
Gln Tyr Ile Leu Lys Val Gly Lys Gly Glu Ala Thr Gln Cys Ile Ser
                325                 330                 335
Gly Phe Thr Ala Met Asp Ala Thr Leu Leu Gly Pro Leu Trp Ile Leu
            340                 345                 350
Gly Asp Val Phe Met Arg Pro Tyr His Thr Val Phe Asp Tyr Gly Asn
355                 360                 365
Leu Leu Val Gly Phe Ala Glu Ala Ala
    370                 375

<210> SEQ ID NO 3
<211> LENGTH: 106
<212> TYPE: PRT
<213> ORGANISM: Artificial sequence
<220> FEATURE:
<223> OTHER INFORMATION: Synthetic construct

<400> SEQUENCE: 3

Val Met Asn Gln Gln Cys Lys Thr Val Val Ser Arg Tyr Gly Arg Asp
1               5                  10                  15
Ile Ile Glu Met Leu Arg Ser Lys Ile Gln Pro Asp Lys Ile Cys Ser
            20                  25                  30
```

```
His Met Lys Leu Cys Thr Phe Asp Gly Ala Arg Asp Val Ser Ser Ile
            35                  40                  45

Ile Glu Ser Val Val Asp Lys Asn Asn Asp Lys Ser Ser Gly Gly Ile
 50                  55                  60

His Asp Glu Met Cys Thr Phe Cys Glu Met Ala Val Val Trp Met Gln
 65                  70                  75                  80

Asn Glu Ile Lys Gln Ser Glu Thr Glu Asp Asn Ile Ile Asn Tyr Ala
                85                  90                  95

Asn Glu Leu Cys Glu His Leu Ser Thr Ser
            100                 105

<210> SEQ ID NO 4
<211> LENGTH: 103
<212> TYPE: PRT
<213> ORGANISM: Artificial sequence
<220> FEATURE:
<223> OTHER INFORMATION: Synthetic construct

<400> SEQUENCE: 4

Val Leu Asn Gln Gln Cys Lys Thr Leu Val Gly Gln Tyr Gly Lys Asn
 1               5                  10                  15

Met Val Gln Met Leu Thr Ser Glu Val Gln Pro Asp Lys Ile Cys Ser
            20                  25                  30

His Met Lys Leu Cys Thr Phe Asp Gly Ala His Asp Val Arg Ser Met
            35                  40                  45

Ile Glu Ser Val Val Asp Lys Asn Asn Asp Lys Ser Ser Gly Gly Glu
 50                  55                  60

Ile Cys Thr Phe Cys Glu Met Ala Leu Val Arg Met Gln Asn Glu Ile
 65                  70                  75                  80

Lys Arg Asn Glu Thr Glu Asp Asn Ile Ile Asn His Val Asn Glu Val
                85                  90                  95

Cys Asp Gln Leu Pro Thr Ser
            100

<210> SEQ ID NO 5
<211> LENGTH: 483
<212> TYPE: PRT
<213> ORGANISM: Cynara cardunculus

<400> SEQUENCE: 5

Met Val Ser Asn Gly Gly Leu Leu Arg Val Gly Leu Lys Lys Arg Lys
 1               5                  10                  15

Val Asp Arg Leu Asp Gln Leu Arg Ala His Gly Val His Met Leu Gly
            20                  25                  30

Asn Ala Arg Lys Asp Phe Gly Phe Arg Arg Thr Leu Arg Asp Ser Gly
            35                  40                  45

Ser Gly Ile Val Ala Leu Thr Asn Asp Arg Asp Thr Ala Tyr Tyr Gly
 50                  55                  60

Glu Ile Gly Ile Gly Thr Pro Pro Gln Asn Phe Ala Val Ile Phe Asp
 65                  70                  75                  80

Thr Gly Ser Ser Asp Leu Trp Val Pro Ser Thr Lys Cys Asp Thr Ser
            85                  90                  95

Leu Ala Cys Val Ile His Pro Arg Tyr Asp Ser Gly Asp Ser Ser Thr
            100                 105                 110

Tyr Lys Gly Asn Gly Thr Thr Ala Ser Ile Gln Tyr Gly Thr Gly Ala
            115                 120                 125

Ile Val Gly Phe Tyr Ser Gln Asp Ser Val Glu Val Gly Asp Leu Val
```

```
                130             135             140
Val Glu His Gln Asp Phe Ile Glu Thr Thr Glu Glu Asp Thr Val
145                 150             155             160

Phe Leu Lys Ser Glu Phe Asp Gly Ile Leu Gly Leu Gly Phe Gln Glu
                165             170             175

Ile Ser Ala Gly Lys Ala Val Pro Val Trp Tyr Asn Met Val Asn Gln
                180             185             190

Gly Leu Val Glu Glu Ala Val Phe Ser Phe Trp Leu Asn Arg Asn Val
                195             200             205

Asp Glu Glu Glu Gly Gly Glu Leu Val Phe Gly Gly Val Asp Pro Asn
                210             215             220

His Phe Arg Gly Asn His Thr Tyr Val Pro Val Thr Arg Lys Gly Tyr
225                 230             235             240

Trp Gln Phe Glu Met Gly Asp Val Leu Ile Gly Asp Lys Ser Ser Gly
                245             250             255

Phe Cys Ala Gly Gly Cys Ala Ala Ile Ala Asp Ser Gly Thr Ser Phe
                260             265             270

Phe Ala Gly Pro Thr Ala Ile Ile Thr Gln Ile Asn Gln Ala Ile Gly
                275             280             285

Ala Lys Gly Val Leu Asn Gln Gln Cys Lys Thr Leu Val Gly Gln Tyr
290                 295             300

Gly Lys Asn Met Val Gln Met Leu Thr Ser Glu Val Gln Pro Asp Lys
305                 310             315             320

Ile Cys Ser His Met Lys Leu Cys Thr Phe Asp Gly Ala His Asp Val
                325             330             335

Arg Ser Met Ile Glu Ser Val Val Asp Lys Asn Asn Asp Lys Ser Ser
                340             345             350

Gly Gly Glu Ile Cys Thr Phe Cys Glu Met Ala Leu Val Arg Met Gln
                355             360             365

Asn Glu Ile Lys Arg Asn Glu Thr Glu Asp Asn Ile Ile Asn His Val
370                 375             380

Asn Glu Val Cys Asp Gln Leu Pro Thr Ser Ser Ala Glu Ser Met Val
385                 390             395             400

Asp Cys Asn Gly Ile Ser Ser Met Pro Asn Ile Ala Phe Thr Ile Gly
                405             410             415

Ser Lys Leu Phe Glu Val Thr Pro Glu Gln Tyr Ile Tyr Lys Val Gly
                420             425             430

Glu Gly Glu Ala Ala Thr Cys Ile Ser Gly Phe Thr Ala Leu Asp Ile
                435             440             445

Met Ser Pro Gln Gly Pro Ile Trp Ile Leu Gly Asp Met Phe Met Gly
450                 455             460

Pro Tyr His Thr Val Phe Asp Tyr Gly Lys Leu Arg Val Gly Phe Ala
465                 470             475             480

Glu Ala Val

<210> SEQ ID NO 6
<211> LENGTH: 480
<212> TYPE: PRT
<213> ORGANISM: Cynara cardunculus

<400> SEQUENCE: 6

Met Ser Asp Asp Gly Leu Ile Arg Ile Gly Leu Lys Lys Arg Lys Val
1               5               10              15

Asp Arg Ile Asp Gln Leu Arg Gly Arg Arg Ala Leu Met Glu Gly Asn
```

-continued

```
            20                  25                  30
Ala Arg Lys Asp Phe Gly Phe Arg Gly Thr Val Arg Asp Ser Gly Ser
            35                  40                  45
Ala Val Val Ala Leu Thr Asn Asp Arg Asp Thr Ser Tyr Phe Gly Glu
50                  55                  60
Ile Gly Ile Gly Thr Pro Pro Gln Lys Phe Thr Val Ile Phe Asp Thr
65                  70                  75                  80
Gly Ser Ser Val Leu Trp Val Pro Ser Lys Cys Ile Asn Ser Lys
                85                  90                  95
Ala Cys Arg Ala His Ser Met Tyr Glu Ser Ser Asp Ser Ser Thr Tyr
            100                 105                 110
Lys Glu Asn Gly Thr Ser Gly Ala Ile Ile Tyr Gly Thr Gly Ser Ile
            115                 120                 125
Thr Gly Phe Phe Ser Gln Asp Ser Val Thr Ile Gly Asp Leu Val Val
            130                 135                 140
Lys Glu Gln Asp Phe Ile Glu Ala Thr Asp Glu Ala Asp Asn Val Phe
145                 150                 155                 160
Leu His Arg Leu Phe Asp Gly Ile Leu Gly Leu Ser Phe Gln Thr Ile
                165                 170                 175
Ser Val Pro Val Trp Tyr Asn Met Val Asn Gln Gly Leu Val Lys Glu
            180                 185                 190
Arg Arg Phe Ser Phe Trp Leu Asn Arg Asn Val Asp Glu Glu Glu Gly
            195                 200                 205
Gly Glu Leu Val Phe Gly Gly Leu Asp Pro Asn His Phe Arg Gly Asp
            210                 215                 220
His Thr Tyr Val Pro Val Thr Tyr Gln Tyr Tyr Trp Gln Phe Gly Ile
225                 230                 235                 240
Gly Asp Val Leu Ile Gly Asp Lys Ser Thr Gly Phe Cys Ala Pro Gly
                245                 250                 255
Cys Gln Ala Phe Ala Asp Ser Gly Thr Ser Leu Leu Ser Gly Pro Thr
            260                 265                 270
Ala Ile Val Thr Gln Ile Asn His Ala Ile Gly Ala Asn Gly Val Met
            275                 280                 285
Asn Gln Gln Cys Lys Thr Val Val Ser Arg Tyr Gly Arg Asp Ile Ile
            290                 295                 300
Glu Met Leu Arg Ser Lys Ile Gln Pro Asp Lys Ile Cys Ser His Met
305                 310                 315                 320
Lys Leu Cys Thr Phe Asp Gly Ala Arg Asp Val Ser Ser Ile Ile Glu
                325                 330                 335
Ser Val Val Asp Lys Asn Asn Asp Lys Ser Ser Gly Gly Ile His Asp
            340                 345                 350
Glu Met Cys Thr Phe Cys Glu Met Ala Val Val Trp Met Gln Asn Glu
            355                 360                 365
Ile Lys Gln Ser Glu Thr Glu Asp Asn Ile Ile Asn Tyr Ala Asn Glu
            370                 375                 380
Leu Cys Glu His Leu Ser Thr Ser Ser Glu Glu Leu Gln Val Asp Cys
385                 390                 395                 400
Asn Thr Leu Ser Ser Met Pro Asn Val Ser Phe Thr Ile Gly Gly Lys
                405                 410                 415
Lys Phe Gly Leu Thr Pro Glu Gln Tyr Ile Leu Lys Val Gly Lys Gly
            420                 425                 430
Glu Ala Thr Gln Cys Ile Ser Gly Phe Thr Ala Met Asp Ala Thr Leu
            435                 440                 445
```

```
Leu Gly Pro Leu Trp Ile Leu Gly Asp Val Phe Met Arg Pro Tyr His
    450                 455                 460

Thr Val Phe Asp Tyr Gly Asn Leu Leu Val Gly Phe Ala Glu Ala Ala
465                 470                 475                 480
```

<210> SEQ ID NO 7
<211> LENGTH: 37
<212> TYPE: DNA
<213> ORGANISM: Artificial sequence
<220> FEATURE:
<223> OTHER INFORMATION: Synthetic construct

<400> SEQUENCE: 7
ctcgagaaaa gaatggtctc caacggcgga ttgcttc          37

<210> SEQ ID NO 8
<211> LENGTH: 37
<212> TYPE: DNA
<213> ORGANISM: Artificial sequence
<220> FEATURE:
<223> OTHER INFORMATION: Synthetic construct

<400> SEQUENCE: 8
gtcgactcaa actgcttctg caaatcccac tcgtaac          37

<210> SEQ ID NO 9
<211> LENGTH: 4
<212> TYPE: PRT
<213> ORGANISM: Cynara cardunculus

<400> SEQUENCE: 9

Ala Glu Ala Ala
1

<210> SEQ ID NO 10
<211> LENGTH: 4
<212> TYPE: PRT
<213> ORGANISM: Cynara cardunculus

<400> SEQUENCE: 10

Ala Glu Ala Val
1

<210> SEQ ID NO 11
<211> LENGTH: 504
<212> TYPE: PRT
<213> ORGANISM: Cynara cardunculus

<400> SEQUENCE: 11

```
Met Gly Thr Ser Ile Lys Ala Asn Val Leu Ala Leu Phe Leu Phe Tyr
1               5                   10                  15

Leu Leu Ser Pro Thr Val Phe Ser Val Ser Asp Asp Gly Leu Ile Arg
            20                  25                  30

Ile Gly Leu Lys Lys Arg Lys Val Asp Arg Ile Asp Gln Leu Arg Gly
        35                  40                  45

Arg Arg Ala Leu Met Glu Gly Asn Ala Arg Lys Asp Phe Gly Phe Arg
    50                  55                  60

Gly Thr Val Arg Asp Ser Gly Ser Ala Val Val Ala Leu Thr Asn Asp
65                  70                  75                  80

Arg Asp Thr Ser Tyr Phe Gly Glu Ile Gly Ile Gly Thr Pro Pro Gln
                85                  90                  95
```

```
Lys Phe Thr Val Ile Phe Asp Thr Gly Ser Ser Val Leu Trp Val Pro
                100                 105                 110

Ser Ser Lys Cys Ile Asn Ser Lys Ala Cys Arg Ala His Ser Met Tyr
            115                 120                 125

Glu Ser Ser Asp Ser Ser Thr Tyr Lys Glu Asn Gly Thr Phe Gly Ala
        130                 135                 140

Ile Ile Tyr Gly Thr Gly Ser Ile Thr Gly Phe Phe Ser Gln Asp Ser
145                 150                 155                 160

Val Thr Ile Gly Asp Leu Val Val Lys Glu Gln Asp Phe Ile Glu Ala
                165                 170                 175

Thr Asp Glu Ala Asp Asn Val Phe Leu His Arg Leu Phe Asp Gly Ile
            180                 185                 190

Leu Gly Leu Ser Phe Gln Thr Ile Ser Val Pro Val Trp Tyr Asn Met
        195                 200                 205

Leu Asn Gln Gly Leu Val Lys Glu Arg Arg Phe Ser Phe Trp Leu Asn
210                 215                 220

Arg Asn Val Asp Glu Glu Gly Gly Glu Leu Val Phe Gly Gly Leu
225                 230                 235                 240

Asp Pro Asn His Phe Arg Gly Asp His Thr Tyr Val Pro Val Thr Tyr
                245                 250                 255

Gln Tyr Tyr Trp Gln Phe Gly Ile Gly Asp Val Leu Ile Gly Asp Lys
            260                 265                 270

Ser Thr Gly Phe Cys Ala Pro Gly Cys Gln Ala Phe Ala Asp Ser Gly
        275                 280                 285

Thr Ser Leu Leu Ser Gly Pro Thr Ala Ile Val Thr Gln Ile Asn His
290                 295                 300

Ala Ile Gly Ala Asn Gly Val Met Asn Gln Gln Cys Lys Thr Val Val
305                 310                 315                 320

Ser Arg Tyr Gly Arg Asp Ile Ile Glu Met Leu Arg Ser Lys Ile Gln
                325                 330                 335

Pro Asp Lys Ile Cys Ser His Met Lys Leu Cys Thr Phe Asp Gly Ala
            340                 345                 350

Arg Asp Val Ser Ser Ile Ile Glu Ser Val Val Asp Lys Asn Asn Asp
        355                 360                 365

Lys Ser Ser Gly Gly Ile His Asp Glu Met Cys Thr Phe Cys Glu Met
370                 375                 380

Ala Val Val Trp Met Gln Asn Glu Ile Lys Gln Ser Glu Thr Glu Asp
385                 390                 395                 400

Asn Ile Ile Asn Tyr Ala Asn Glu Leu Cys Glu His Leu Ser Thr Ser
                405                 410                 415

Ser Glu Glu Leu Gln Val Asp Cys Asn Thr Leu Ser Ser Met Pro Asn
            420                 425                 430

Val Ser Phe Thr Ile Gly Gly Lys Lys Phe Gly Leu Thr Pro Glu Gln
        435                 440                 445

Tyr Ile Leu Lys Val Gly Lys Gly Glu Ala Thr Gln Cys Ile Ser Gly
450                 455                 460

Phe Thr Ala Met Asp Ala Thr Leu Leu Gly Pro Leu Trp Ile Leu Gly
465                 470                 475                 480

Asp Val Phe Met Arg Pro Tyr His Thr Val Phe Asp Tyr Gly Asn Leu
                485                 490                 495

Leu Val Gly Phe Ala Glu Ala Ala
            500
```

```
<210> SEQ ID NO 12
<211> LENGTH: 506
<212> TYPE: PRT
<213> ORGANISM: Cynara cardunculus

<400> SEQUENCE: 12
```

Met Gly Thr Pro Ile Lys Ala Ser Leu Leu Ala Leu Phe Leu Phe Phe
1               5                   10                  15

Leu Leu Ser Pro Thr Ala Phe Ser Val Ser Asn Gly Gly Leu Leu Arg
            20                  25                  30

Val Gly Leu Lys Lys Arg Lys Val Asp Arg Leu Asp Gln Leu Arg Ala
        35                  40                  45

His Gly Val His Met Leu Gly Asn Ala Arg Lys Asp Phe Gly Phe Arg
    50                  55                  60

Arg Thr Leu Ser Asp Ser Gly Ser Gly Ile Val Ala Leu Thr Asn Asp
65                  70                  75                  80

Arg Asp Thr Ala Tyr Tyr Gly Glu Ile Gly Ile Gly Thr Pro Pro Gln
                85                  90                  95

Asn Phe Ala Val Ile Phe Asp Thr Gly Ser Ser Asp Leu Trp Val Pro
            100                 105                 110

Ser Thr Lys Cys Asp Thr Ser Leu Ala Cys Val Ile His Pro Arg Tyr
        115                 120                 125

Asp Ser Gly Asp Ser Ser Thr Tyr Lys Gly Asn Gly Thr Thr Ala Ser
    130                 135                 140

Ile Gln Tyr Gly Thr Gly Ala Ile Val Gly Phe Tyr Ser Gln Asp Ser
145                 150                 155                 160

Val Glu Val Gly Asp Leu Val Val Glu His Gln Asp Phe Ile Glu Thr
                165                 170                 175

Thr Glu Glu Asp Asp Thr Val Phe Leu Lys Ser Glu Phe Asp Gly Ile
            180                 185                 190

Leu Gly Leu Gly Phe Gln Glu Ile Ser Ala Gly Lys Ala Val Pro Val
        195                 200                 205

Trp Tyr Asn Met Val Asn Gln Gly Leu Val Glu Glu Ala Val Phe Ser
    210                 215                 220

Phe Trp Leu Asn Arg Asn Val Asp Glu Glu Gly Glu Leu Val
225                 230                 235                 240

Phe Gly Gly Val Asp Pro Asn His Phe Arg Gly Asn His Thr Tyr Val
                245                 250                 255

Pro Val Thr Arg Lys Gly Tyr Trp Gln Phe Glu Met Gly Asp Val Leu
            260                 265                 270

Ile Gly Asp Lys Ser Ser Gly Phe Cys Ala Gly Gly Cys Ala Ala Ile
        275                 280                 285

Ala Asp Ser Gly Thr Ser Phe Phe Ala Gly Pro Thr Ala Ile Ile Thr
    290                 295                 300

Gln Ile Asn Gln Ala Ile Gly Ala Lys Gly Val Leu Asn Gln Gln Cys
305                 310                 315                 320

Lys Thr Leu Val Gly Gln Tyr Gly Lys Asn Met Ile Gln Met Leu Thr
                325                 330                 335

Ser Glu Val Gln Pro Asp Lys Ile Cys Ser His Met Lys Leu Cys Thr
            340                 345                 350

Phe Asp Gly Ala His Asp Val Arg Ser Met Ile Glu Ser Val Val Asp
        355                 360                 365

Lys Asn Asn Asp Lys Ser Ser Gly Gly Glu Ile Cys Thr Phe Cys Glu
    370                 375                 380

-continued

```
Met Ala Leu Val Arg Met Gln Asn Glu Ile Lys Arg Asn Glu Thr Glu
385                 390                 395                 400

Asp Asn Ile Ile Asn His Val Asn Glu Val Cys Asp Gln Leu Pro Thr
                405                 410                 415

Ser Ser Ala Glu Ser Ile Val Asp Cys Asn Gly Ile Ser Ser Met Pro
            420                 425                 430

Asn Ile Ala Phe Thr Ile Gly Ser Lys Leu Phe Glu Val Thr Pro Glu
        435                 440                 445

Gln Tyr Ile Tyr Lys Val Gly Glu Gly Glu Ala Ala Thr Cys Ile Ser
    450                 455                 460

Gly Phe Thr Ala Leu Asp Ile Met Ser Pro Gln Gly Pro Ile Trp Ile
465                 470                 475                 480

Leu Gly Asp Met Phe Met Gly Pro Tyr His Thr Val Phe Asp Tyr Gly
            485                 490                 495

Lys Leu Arg Val Gly Phe Ala Glu Ala Val
            500             505
```

ASPARTIC PROTEASES

RELATED APPLICATIONS

This application is a 35 U.S.C. § 371 national phase application of PCT/PT2014/000018, filed Mar. 19, 2014 (WO/2014/148932). PCT/PT2014/000018 claims priority to GB Application Serial No. 1305023.2, filed Mar. 19, 2013, which is incorporated herein by reference in its entirety.

FIELD OF THE INVENTION

The present invention relates to aspartic proteases and particularly to aspartic proteases from plants.

Incorporated by reference herein in its entirety is the Sequence Listing entitled "Sequence-List.txt", created Oct. 28, 2015, size of 27 kilobytes.

BACKGROUND TO THE INVENTION

The human epidermis is composed of five layers of stratified epithelial cells and is an organ in constant renewal. New cells are formed in the basal layer and after a differentiation process the cells reach the outermost layer of the skin. Renewal and maintenance requires the cell shedding of corneocytes from the stratum corneum (SC). Aging and certain skin diseases can disturb this process leading to a decrease in desquamation rate, resulting in an increase in thickness of the SC and in skin scales formation.

Skin desquamation is the shedding of corneocytes from the stratum corneum (SC), and is part of the self-renewal and maintenance of the skin. Desquamation or exfoliation of epidermal layers of human skin induces an increased rate of epidermal cell renewal. Desquamation of corneocytes from epidermis requires the enzymatic degradation of corneodesmosome structures, composed of corneodesmosin, desmoglein-1 and desmocolin-1 proteins. Several serine, cysteine and aspartic proteases participate in this exfoliation process including cathepsin D, cathepsin E and SASpase.

Compositions comprising the acid protease pepsin, and the stratum corneum trypsin-like serine proteases have been proposed for a number of uses including improving the texture or appearance of the skin, enhancing epidermal exfoliation, inducing skin desquamation and causing cell renewal (U.S. Pat. No. 6,656,701; WO95/07688). The acid proteases described in U.S. Pat. No. 6,656,701 exhibit peptidyl hydrolase (proteolytic) activity below the average pH of the surface of the skin, but which are significantly inactive at a pH greater than the average pH of the surface of the skin (about pH 5.5 for humans). The aspartic protease cathepsin D is also thought to facilitate desmosomal degradation, and has been exploited in some cosmetic/cosmeceutical preparations, for example purified oligosaccharides extracted from the fruit of prickly pear (Opuntia ficus indicia) have been used in facial acid peel treatments to enhance cathepsin D activity.

Aspartic proteases are peptidases present in animals, plants, fungi and viruses and exhibit a wide range of functions and activities, including: mammalian digestion e.g. chymosin and pepsin A, activation and degradation of polypeptide hormones and growth factors e.g. cathepsin D, regulation of blood pressure e.g. rennin, degradation of haemoglobin by parasites e.g. plasmepsins, proteolytic processing of the HIV polyprotein e.g. retropepsin, involvement in pollen-pistil interactions in plants e.g. Cardosin A.

Aspartic proteases are synthesised as preproenzymes and contain a signal peptide, which is cleaved resulting in a proenzyme which can be secreted and activated autocatalytically. Generally, aspartic proteases consist of a single peptide chain of approximately 320-360 amino acid residues, composed mainly of β-strand structures arranged into two lobes. The catalytic site of the enzyme is located between these two lobes, each containing an aspartate residue which are within hydrogen-bonding distance of each other and act together to activate a water molecule which results in cleavage of the substrate peptide bond (via nucleophilic attack).

Plant aspartic proteases differ from other aspartic proteases in that they comprise a Plant Specific Insert which is cleaved out during protein maturation, besides a signal peptide (responsible for translocation to the ER); a prosegment of 40-50 amino acid residues (involved in the correct folding, stabilisation and sorting of the enzyme); and a mature enzyme possessing two catalytic sequence motifs. The two catalytic aspartate residues in plant aspartic proteases are contained within Asp-Thr-Gly and Asp-Ser-Gly motifs.

Plant Specific Insert (PSI)

Many plant aspartic proteases differ from their mammalian and microbial counterparts by the presence of a plant-specific insert (PSI), typically having about 104 amino acids. In phytepsin, from barley, removal of the PSI led to secretion of the mutated phytepsin when expressed in Tobacco protoplasts, whilst retaining enzymatic activity[4]. The presence of PSI was shown to be at least necessary for vacuolar sorting[4].

Vacuolar Sorting

The final destination of a protein after synthesis is a highly complex and regulated process and is usually dependent on the presence of specific targeting information (e.g. sorting signals, post-translational modifications) which is specifically recognized by receptors that target nascent proteins to their final localizations in the cell[1].

One of the most complex biosynthetic routes is the secretory pathway. In a very simplified way, this system comprises several membrane-bound subcellular compartments and proteins are exchanged between these compartments by vesicle trafficking. Proteins resident in the endoplasmic reticulum (ER), Golgi apparatus, vacuoles or plasma membrane/extracellular matrix have to enter this endomembrane system and some of them undergo processing and post-translational modifications along their passage through the ER and Golgi network. Targeting to ER is determined cotranslationally by the presence of a signal peptide at the N-terminus of a nascent protein[1]. Although recent evidence indicates that the system may be more complex than first expected[2], it is still generally accepted that proteins are actively sorted to vacuoles, meaning that they contain specific vacuolar sorting signals (VSS's).

Different types of vacuolar sorting signals (VSS's) have been identified[1,3]. Even though no consensus sequence has been yet defined for these signals they are currently divided into three categories: sequence-specific VSS (ssVSS's) which comprise N-terminal propeptides (e.g. sporamin) or internal sequences (e.g. ricin); C-terminal propeptides (CT-PP's) (e.g. lectin and chitinase) and physical structure VSS (psVSS's) [e.g. plant specific insert (PSI) of phytepsin][3]. Given the number of soluble vacuolar proteins that lack these types of VSS's, it is expected that novel motifs for vacuolar sorting are yet to be identified.

The ability to manipulate protein sorting is particularly important if considering high value-protein expression in heterologous or homologous systems. Specifically sorting a selected protein to storage vacuoles may be highly advantageous for accumulation of large quantities of recombinant proteins and, thereby, increase the food value of a plant. Conversely, redirecting a native vacuolar protein for secretion may be particularly useful considering, for example, expression in heterologous systems like yeasts where protein secretion into the media greatly facilitates recombinant protein handling and purification.

The relevance of these vacuolar sorting signals in various applications is confirmed by different issued patents: U.S. Pat. Nos. 6,9723,504, 7,368,6285, 5,360,7266 and 60,546,377, where the last two describe the VSS's of lectin and chitinase, respectively.

Typical aspartic proteases are widely distributed in plants and have been purified from a variety of tissues. In general, these enzymes share high levels of amino acid sequence identity (over 60%) and the majority of them accumulate inside plant vacuoles. However, there are exceptions to this intracellular localization and several plant aspartic proteases were shown to be extracellular.

SUMMARY OF THE INVENTION

The inventors have discovered that plant aspartic proteases, in particular Cardosins, and particularly Cardosin B, show skin desquamation activity, without affecting cellular viability. These plant aspartic proteases have enhanced ability to induce skin desquamation compared to mammalian aspartic proteases, including Cathepsin D.

The present invention therefore provides a method of medical treatment, the method comprising administering a plant aspartic protease to a subject in need of such treatment. The method may be for the treatment of a skin disorder. The method preferably involves inducing skin desquamation in the subject. The subject is preferably one suffering from at least one of xerosis, eczema, acne, psoriasis or ichthyosis, and the method involves the treatment of at least one of xerosis, eczema, acne, psoriasis or ichthyosis. The plant aspartic protease may be a mutant that lacks a functional plant specific insert (PSI) domain. The plant aspartic protease may be a Cardosin, such as one of Cardosin B or Cardosin A, or a mutant thereof. The plant aspartic protease may have at least 70% sequence identity to SEQ ID NO: 1, or SEQ ID NO: 2.

The present invention also provides the use of a plant aspartic protease in the manufacture of a medicament for treating a skin disorder. The treatment preferably involves inducing skin desquamation. The medicament may be provided to treat a skin disorder, such as xerosis, eczema, acne, psoriasis or ichthyosis. The plant aspartic protease may be a mutant that lacks a functional plant specific insert (PSI) domain. The plant aspartic protease may be a Cardosin, such as one of Cardosin B or Cardosin A, or a mutant thereof. The plant aspartic protease may have at least 70% sequence identity to SEQ ID NO: 1, or SEQ ID NO: 2.

In another aspect of the present invention a plant aspartic protease is provided for use in a method for treatment of the human or animal body by therapy. This may involve the treatment of a skin disorder and may preferably involve the induction of skin desquamation. As such, the plant aspartic protease may be provided for use in the treatment of at least one of xerosis, eczema, acne, psoriasis or ichthyosis. The plant aspartic protease may be a mutant that lacks a functional plant specific insert (PSI) domain. The plant aspartic protease may be a Cardosin, such as one of Cardosin B or Cardosin A, or a mutant thereof. The plant aspartic protease may have at least 70% sequence identity to SEQ ID NO: 1, or SEQ ID NO: 2.

In a further aspect of the present invention a cosmetic method for improving the appearance of the skin is provided, the method comprising administering a plant aspartic protease to the skin. The method may involve the induction of skin desquamation. The plant aspartic protease may be a mutant that lacks a functional plant specific insert (PSI) domain. The plant aspartic protease may be a Cardosin, such as one of Cardosin B or Cardosin A, or a mutant thereof. The plant aspartic protease may have at least 70% sequence identity to SEQ ID NO: 1, or SEQ ID NO: 2.

In another aspect of the present invention a composition is provided, the composition comprising an isolated plant aspartic protease. The plant aspartic protease may lack a functional plant specific insert (PSI) domain. The plant aspartic protease may be a Cardosin, such as one of Cardosin B or Cardosin A, or a mutant thereof. The plant aspartic protease may have at least 70% sequence identity to SEQ ID NO: 1, or SEQ ID NO: 2. The composition may be formulated for topical administration. The composition may be formulated as a pharmaceutical composition or medicament. Alternatively, the composition may be formulated as a cosmetic composition.

The inventors have also determined that the normal VSS function of the ~100 amino acid plant specific insert (PSI) may be inactivated by recombinant DNA manipulation to enhance secretion of plant aspartic proteases in either homologous or heterologous expression systems (preferably heterologous, non-plant, expression systems), whilst retaining the aspartic protease activity of the secreted protein. Thus, the inventors have provided a novel and advantageous means of producing high volumes of plant aspartic proteases in a form that is convenient to isolate and purify.

Accordingly, the present invention also provides methods for the expression in cells of mutant plant aspartic proteases modified such that the PSI domain is inactivated, the expression preferably being in non-plant eukaryotic cells. Preferably, the mutant plant aspartic proteases retain their protease activity.

In one aspect of the present invention an isolated mutant Cardosin plant aspartic protease is provided, wherein the Cardosin plant aspartic protease is mutated such that it lacks a functional plant specific insert (PSI) domain. The Cardosin plant aspartic protease may have an amino acid sequence having at least 70% sequence identity to SEQ ID NO: 1, or SEQ ID NO: 2.

In another aspect of the present invention a method for producing a mutant plant aspartic protease is provided, the method comprising expressing, in a cell that is preferably not a plant cell of plant protoplast, a mutant plant aspartic protease, wherein the plant aspartic protease is mutated such that it lacks a functional plant specific insert (PSI) domain.

The method preferably involves secretion of the mutant plant aspartic protease from the cell, the method further comprising obtaining or collecting mutant plant aspartic protease secreted from the cell. Obtaining or collection of plant aspartic protease may involve partitioning of protein material from the culture media/fermentation broth and isolation of the plant aspartic protease fraction.

The nucleotide sequence encoding the mutant plant aspartic protease may be provided on a vector such that it is expressed from a vector contained in the cell. Alternatively, the nucleotide sequence encoding the mutant plant aspartic protease may be incorporated in the genome of the cell and expressed from the genome.

The cell is preferably a eukaryotic cell. In some embodiments it is a fungal cell, e.g. a yeast cell. The cell is optionally not a plant cell or plant protoplast.

The method may further comprise the step of mixing mutant plant aspartic protease obtained from said cell with a carrier, adjuvant or diluent to form a product comprising a composition containing said mutant plant aspartic protease.

In some aspects the vector comprises nucleic acid encoding a plant aspartic protease mutant lacking a functional plant specific insert (PSI) domain. Preferably, the plant aspartic protease mutant is either (i) the polypeptide of SEQ ID NO: 1, or SEQ ID NO: 2, or (ii) a polypeptide having at least 70% sequence identity to SEQ ID NO: 1, or SEQ ID NO: 2. The nucleic acid of (i) or (ii) is preferably operably linked to a regulatory sequence to control expression of the nucleic acid in a host cell, and may thereby form an expression cassette. A cell comprising the vector is also provided.

In other aspects a cell is provided having a genome modified to contain nucleic acid encoding a plant aspartic protease mutant lacking a functional plant specific insert (PSI) domain. Preferably, the plant aspartic protease mutant is either (i) the polypeptide of SEQ ID NO: 1, or SEQ ID NO: 2, or (ii) a polypeptide having at least 70% sequence identity to SEQ ID NO: 1, or SEQ ID NO: 2. The nucleic acid of (i) or (ii) is preferably operably linked to a regulatory sequence to control expression of the nucleic acid, and may thereby form an expression cassette In a further aspect of the present invention a method for promoting accumulation of a polypeptide of interest in the vacuole of a cell, optionally a plant cell or plant protoplast, is provided, the method comprising expressing a polypeptide construct in the cell, the polypeptide construct comprising the amino acid sequence of the polypeptide of interest covalently linked to the amino acid sequence of a PSI domain. The PSI domain may have at least 70% sequence identity to SEQ ID NO: 3, or SEQ ID NO: 4.

In some aspects a vector is provided comprising nucleic acid encoding the polypeptide construct. The nucleic acid is preferably operably linked to a regulatory sequence to control expression of the nucleic acid in a host cell, and may thereby form an expression cassette. A cell comprising the vector is also provided.

In other aspects a cell having a genome modified to contain nucleic acid encoding the polypeptide construct is provided. The nucleic acid is preferably operably linked to a regulatory sequence to control expression of the nucleic acid in the cell, and may thereby form an expression cassette.

The present invention therefore also provides a plant aspartic protease that is modified so as to lack a functional plant specific insert (PSI) domain. The PSI domain may be entirely deleted, or partially deleted. For example, at least 60, at least 65, at least 70, at least 75, at least 80, at least 85, at least 90, at least 95, at least 100 or more amino acids of the PSI domain may be deleted. The number of amino acids deleted may be calculated by comparing the plant aspartic protease sequence or PSI domain sequence to the sequence of an unmodified plant aspartic protease, such as a wild-type plant aspartic protease. The PSI domain may be wholly or partially replaced with a linker, such as a linker of 1, 2, 3, 4, 5, 6, 7, 8, 9, 10 or more amino acid residues. The amino acids of the linker may be all the same, for example, they may all be glycine residues. Alternatively, the linker may comprise a plurality of different amino acids. However, this linker does not comprise all, or substantially all, the amino acid residues of the functional PSI domain.

The modification to the PSI domain may confer altered trafficking on the plant aspartic protease. For example, trafficking of the plant aspartic protease within a cell may be modified as compared to the trafficking of a plant aspartic protease which does not have a modified PSI domain, such as a wild type plant aspartic protease. The plant aspartic proteases according to the invention have caseinolytic activity.

The plant aspartic protease according to the invention may have a pro segment. The N-terminal of the plant aspartic protease may not be modified with respect to, or different to, wild-type plant aspartic protease.

The plant aspartic protease according to the invention may be modified at the C-terminus. For example, the plant aspartic protease according to the invention may not have sequence AEAA or AEAV at the C-terminus.

The plant aspartic protease of the invention may be a modified cardosin, cyprosin, cenprosin, phytepsin, or cynarase. It may have a sequence of at least 70%, at least 75%, at least 80%, at least 85%, at least 90%, at least 95% or at least 98% sequence identity to a known cardosin, cyprosin, cenprosin, phytepsin, or cynarase sequence. In some cases, the plant aspartic protease may be a cardosin, such as cardosin A or cardosin B. In some cases, the plant aspartic protease according to the invention is cardosin B.

In some cases, the plant aspartic protease according to the invention has at least 70% identity to SEQ ID NO: 1 or SEQ ID NO: 2. In some cases, it has at least 75%, at least 80%, at least 85%, at least 90%, at least 95% or at least 98% identity to SEQ ID NO: 1 or SEQ ID NO: 2.

A plant aspartic protease according to the invention may have been expressed in a eukaryotic cell. For example, the plant aspartic protease may have been expressed in a yeast cell, for example a *Kluyveromyces lactis* cell. In some cases, the plant aspartic protease according to the invention has not been produced in a plant protoplast. In some cases the plant aspartic protease has not been produced in *E. coli*.

The invention also provides nucleic acid encoding a plant aspartic protease according to the invention. For example, nucleic acid encoding a plant aspartic protease which lacks a functional PSI domain; a polypeptide having amino acid sequence SEQ ID NO: 1, or SEQ ID NO: 2, or a polypeptide having at least 70% sequence identity to SEQ ID NO: 1, or SEQ ID NO: 2, wherein the polypeptide lacks a functional plant specific insert (PSI) domain. A vector comprising the nucleic acid is also provided, for example a yeast expression vector.

Also provided is a cell which encodes a plant aspartic protease according to the invention. The cell may have a genome modified to encode the plant aspartic protease, or may include a vector that encodes the plant aspartic protease. The cell may have nucleic acid, for example, its genome may be modified to include nucleic acid, which encodes a plant aspartic protease which lacks a functional PSI domain; the polypeptide of SEQ ID NO: 1, or SEQ ID NO: 2, or a polypeptide having at least 70% sequence identity to SEQ ID NO: 1, or SEQ ID NO: 2, wherein the polypeptide encoded lacks a functional plant specific insert (PSI) domain. The cell may be a yeast cell, such as *Kluyveromyces lactis*.

The invention also provides a method for producing a plant aspartic protease in which a cell, preferably a cell which is not a plant cell, or a plant protoplast, or an *E. coli*, which expresses a plant aspartic protease which lacks a functional plant specific insert (PSI) domain.

In some methods the plant aspartic protease is secreted from the cell, and the method may comprise collecting the plant aspartic protease that has been secreted from the cell, for example by partitioning the secreted plant aspartic protease from other components secreted from the cell or otherwise contained within the media in which the cells are growing. The method may comprise expressing the plant aspartic protease from a vector contained within the cell, or from the genome of the cell. The cell may be a eukaryotic cell. The cell may be a fungal cell such as a yeast cell, for example *Kluyveromyces lactis*.

DETAILED DESCRIPTION

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which:

FIG. 7. Sequences of Cardosins B and A with and without PSI sequence, PSI sequences, and sequences used in the examples.

PREFERRED EMBODIMENTS OF THE INVENTION

Figure 1:
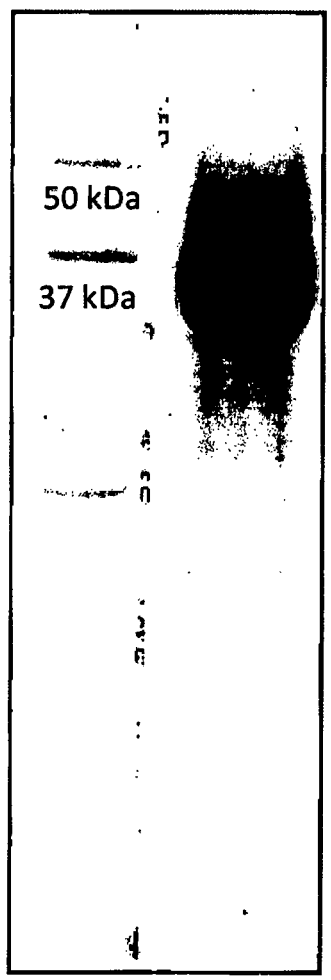
FIG. 1. SDS-PAGE gel electrophoresis of enzyme purified from *K. lactis* (pCBΔPSI, hereby named pAP).

The inventors have discovered that plant aspartic proteases, in particular Cardosins, and particularly Cardosin B, show skin desquamation activity, without affecting cellular viability.

Desquamation is the shedding of the skin, in particular the stratum corneum, the outermost layer of the epidermis. Desquamation occurs normally, under non-pathological conditions, and may also result from injury or disease of the akin, for example following the rash of measles or sunburn.

Desquamation of corneocytes from epidermis requires the enzymatic degradation of corneodesmosome structures, composed of corneodesmosin, desmoglein-1 and desmocolin-1 proteins. It is thought that the process of desquamation involves proteolytic degradation of desmosomes, causing the cohesive links between the cells to break down thereby allowing detachment of peripheral corneocytes from the surface of the stratum corneum. Several serine, cysteine and aspartic proteases participate in this exfoliation process, including cathepsin D, cathepsin E and SASpase. For example, WO95/07688 discloses a role for stratum corneum trypsin-like enzymes (serine proteases) from skin in the induction of skin desquamation.

The inventors have shown that plant aspartic proteases, particularly Cardosins, and particularly Cardosin B, have enhanced ability to induce skin desquamation compared to mammalian aspartic proteases, including Cathepsin D. The plant aspartic proteases of the invention induce greater skin desquamation over a given period of time than the level of skin desquamation induced by Cathepsin D. The amount of skin desquamation may be measured by any suitable method known in the art, such as by counting the number of detached cells on a hemocytometer. The number of detached cells may be measured after 1 hour, after 2 hours, after 3 hours, after 4 hours, after 5 hours or after 6 hours or more of exposure to the aspartic protease.

The plant aspartic proteases according to the invention preferably do not reduce cell viability, i.e. cell viability is not significantly different to the cell viability observed when the cells are not exposed to a plant aspartic protease according to the invention. Thus, the plant aspartic proteases according to the invention do not exhibit significant cytotoxic activity. Cell viability may be measured by any method known in the art, such as by MTT assay.

The plant aspartic proteases of the present invention exhibit skin desquamation activity over a broad range of pH values. Preferably, the plant aspartic proteases according to the invention are active at mildly acidic pH. The plant aspartic proteases according to the invention may be active between about pH 3 and about pH 7 between about pH 4 and about pH 7, between about pH 4 and about pH 5, between about pH 4 and about pH 6, between about pH 5 and about pH 7, between about pH 5 and about pH 6 or between about pH 6 and about pH 7.

Therapeutic Applications

The compounds and compositions of the present invention are useful in the treatment of a wide range of diseases and conditions. In particular, the compounds and compositions of the present invention are useful in the treatment of disorders, diseases and conditions of the skin and find application in the treatment of fibrosis (including post-surgical fibrosis), tissue adhesion formation, and scar formation. The compounds and compositions of the invention are useful in the treatment of acne, eczema, ichthyosis and psoriasis. Compounds, compositions and methods described herein may be used to enhance epidermal exfoliation and/or enhance epidermal cell renewal, and to improve the texture and/or appearance of the skin.

The plant aspartic proteases and compositions disclosed herein are useful for the treatment of any condition for which the induction or enhancement of skin desquamation would be beneficial. In particular for treating xerosis (dryness of the skin, such as dry skin resulting from Indinavir treatment of HIV), acne, psoriasis, eczema, and dermal or epidermal proliferations, certain benign or malignant tumor lesions, reactive hyperkeratoses, preventing epidermal and/or dermal atrophy, combating dysfunction of cell proliferation and/or differentiation, and avoiding the effects of HIV medication such as Indinavir.

Acne

Acne is a skin condition which involves plugged pores (blackheads and whiteheads), inflamed pimples (pustules), and deeper lumps (nodules). Acne occurs on the face, as well as the neck, chest, back, shoulders, and upper arms. Although most teenagers get some form of acne, adults in their 20's, 30's, 40's, or even older, can develop acne. Often, acne clears up after several years, even without treatment. Untreated acne can leave permanent scars. To avoid acne scarring, treating acne is important. There are three major factors that contribute to the formation and exacerbation of acne, overproduction of oil (sebum), irregular shedding of dead skin cells resulting in irritation of the hair follicles of skin and buildup of bacteria.

Acne is the most common skin disease of adolescence, affecting over 80% of teenagers (aged 13-18 years) at some point[12]. Estimates of prevalence vary depending on study populations and the method of assessment used. Prevalence of acne in a community Sample of 14- to 16-year-olds in the UK has been recorded as 50%[13]. In a sample of adolescents from schools in New Zealand, acne was present in 91% of males and 79% of females, and in a similar population in Portugal the prevalence was 82%[14]. The number of adults with acne, including people over 25 years, is increasing, although the reasons for this increase are uncertain[15].

Eczema

Eczema (atopic dermatitis) is a particular type of inflammatory reaction of the skin in which there are typically vesicles (tiny blister-like raised areas) in the first stage followed by erythema (reddening), edema (swelling), papules (bumps), and crusting of the skin followed, finally, by lichenification (thickening) and scaling of the skin. Eczema characteristically causes itching and burning of the skin.

Eczema is very common and can first occur at any age. It is frequently chronic and difficult to treat, and it tends to disappear and recur. Itching can be extreme and severe. There are a number of types of eczema. The prevalence of ezcema is high with an estimated 33 million people in the USA alone affected.

Ichthyosis

Ichthyosis vulgaris is a genetic skin disease that is characterised by the presence of excessive amounts of dry surface scales on the skin caused by abnormal epidermal differentiation or metabolism. It is usually most severe over the legs but may also involve the arms, hands, and trunk in some cases. It may also be associated with atopic dermatitis, keratosis pilaris (small bumps on the back of the arms), or other skin disorders. It usually disappears during adulthood, but may recur when elderly.

Other types of ichthyosis include X-linked ichthyosis, ichthyosis lamellaris, epidermolytic hyperkeratosis, harlequin type ichthyosis, Netherton's syndrome and Sjogren-Larsson syndrome, although ichthyosis vulgaris, accounts for 95% of all ichthyosis cases. Hereditary (congenital) ichthyosis vulgaris accounts for more than 95% of cases of ichthyosis vulgaris. It first appears in early childhood. The gene responsible for ichthyosis vulgaris has been mapped to chromosome band 1q21. The product of this gene is a substance called filaggrin (FLG) which may act as the "keratin matrix protein" in cells of the stratum corneum. The inheritance pattern is autosomal dominant. Acquired ichthyosis vulgaris, typically develops in adulthood and results from an internal disease of the use of certain medications. Hereditary ichthyosis vulgaris is a common disease in United States, with a prevalence of approximately 1 case in 300 persons. Because symptoms improve with age, the true prevalence is probably higher. Acquired ichthyosis is extremely rare. Its prevalence in United States is unknown. In the United Kingdom, the incidence of ichthyosis vulgaris was reported to be 1 in 250. In China, ichthyosis vulgaris has a prevalence of 2.29%.

Psoriasis

Psoriasis is a chronic, genetic, non-contagious skin disorder characterised by itchy or sore patches of thick, red skin with silvery scales. The scaly patches caused by psoriasis, called psoriatic plaques, are areas of inflammation and excessive skin production. The disorder is a chronic recurring condition which varies in severity from minor localised patches to complete body coverage. Psoriasis can also cause inflammation of the joints, which is known as psoriatic arthritis. There are a number of forms of the disease. According to the National Institutes of Health (NIH), as many as 7.5 million Americans (approximately 2.2 percent of the population) have psoriasis, with an estimated 125 million being affected globally. Between 150,000 and 260,000 new cases of psoriasis occurring each year. Incidence of psoriasis tends to be affected by the climate and genetic heritage of the population. It is less common in the tropics and in dark-skinned persons, and most common in Caucasians. Total direct and indirect health care costs of psoriasis for patients are calculated at $11.25 billion annually, with work loss accounting for 40% of the cost burden[16]. Approximately 60% of psoriasis patients missed an average of 26 days of work a year due to their illness[17].

Subjects

The subject to be treated (therapeutically or cosmetically) may be any animal or human. The subject is preferably mammalian, more preferably human. The subject may be a non-human mammal, but is more preferably human. The subject may be male or female. The subject may be a patient. Therapeutic and cosmetic uses may be in humans or animals (veterinary use).

Cosmetic Applications

In some aspects the invention relates to a cosmetic treatment comprising the administration of a plant aspartic protease. "Cosmetic" as used herein is non-therapeutic. The cosmetic treatment may be used to improve the appearance and/or texture of the skin. The cosmetic treatment may be used to enhance epidermal exfoliation and/or enhance epidermal cell renewal.

In some aspects the invention relates to a method of cosmetic treatment comprising the administration of a plant aspartic protease. "Cosmetic" as used herein is non-therapeutic. Such methods do not involve the treatment of the human or animal body by therapy. As used herein the term "cosmetic method" does not include a method for treatment of the human or animal body by surgery or therapy, or a diagnostic method practised on the human or animal body according to Article 53(c) EPC.

The subject treated by the cosmetic methods disclosed herein may be a non-human mammal, but is more preferably human. The subject may be male or female. The subject does not require inhibition of induction of skin desquamation for therapeutic benefit. In some cases the subject does not require therapeutic skin desquamation at the site at which the cosmetic treatment is to be applied.

The invention also provides a cosmetic composition comprising a plant aspartic protease. The composition may be used to improve the appearance of the skin. Cosmetic compositions may be formulated similarly to pharmaceutical compositions, as described below. A cosmetically effective amount of a plant aspartic protease may be administered to the subject. That is, an amount of plant aspartic protease effective to induce a cosmetic benefit. This is within the sound judgement of a relevant practitioner, who will appreciate that the appropriate dosages of the active compound or a composition containing the active compound can vary from subject to subject.

Administration

The compound of the invention may be formulated for pharmaceutical administration. Any convenient route of administration may be used, whether systemically, peripherally or topically (i.e. at the site of desired action). Preferably, the compound is formulated for topical administration. In particular embodiments of the invention, the compounds are administered to the skin.

The compound of the invention may be formulated for cosmetic administration. Any convenient route of administration may be used, whether systemically, peripherally or topically (i.e. at the site of desired action). Preferably, the compound is formulated for topical administration. In particular embodiments of the invention, the compounds are administered to the skin.

For therapeutic applications, administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

While it is possible for the active compound to be administered alone, it is preferable to present it as a pharmaceutical or cosmetic formulation (e.g., composition, preparation, medicament) comprising at least one active compound, as defined above, together with one or more other pharmaceutically or cosmetically acceptable ingredients well known to those skilled in the art, including, but not limited to, pharmaceutically or cosmetically acceptable carriers, adjuvants, excipients, diluents, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical and cosmetic compositions, as defined above, and methods of making a pharmaceutical or cosmetic composition comprising admixing at least one active compound, as defined above, together with one or more other pharmaceutically or cosmetically acceptable ingredients well known to those skilled in the art, e.g., carriers, adjuvants, excipients, etc. If formulated as discrete units (e.g., tablets, etc.), each unit contains a predetermined amount (dosage) of the active compound.

The terms "pharmaceutically acceptable" and "cosmetically acceptable" as used herein pertains to compounds, ingredients, materials, compositions, dosage forms, etc., which are, within the scope of sound judgment of the relevant practitioner, suitable for use in contact with the tissues of the subject in question (e.g., human) without excessive toxicity, irritation, allergic response, or other problem or complication, commensurate with a reasonable benefit/risk ratio. Each carrier, adjuvant, excipient, etc. must also be "acceptable" in the sense of being compatible with the other ingredients of the formulation.

Formulations suitable for transdermal administration include gels, pastes, ointments, creams, lotions, and oils, as well as patches, adhesive plasters, bandages, dressings, depots, and reservoirs.

The formulation may be prepared to provide for rapid or slow release; immediate, delayed, timed, or sustained release; or a combination thereof.

Ointments may be prepared using the plant aspartic protease and a paraffinic or a water-miscible ointment base.

Creams may be prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1, 3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Emulsions may be prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

The inventors have demonstrated that plant aspartic proteases of the invention are active at across a range of pH. As such, compounds and compositions of the present invention may be formulated, and/or administered in, neutral, mildly alkaline, or acid buffers, diluents, carriers or adjuvants.

A buffer is a composition which, when topically administered to the skin, temporarily alters the pH of the surface of the skin. An acid buffer may lower the pH of the skin to pH 6.0 of lower, pH 5.5 or lower, pH 5.0 or lower, pH 4.5 or lower, pH 4.0 or lower, pH 3.5 or lower or pH 3.0 or lower. Preferably the pH of the surface of the skin is not lower than pH 2.5 or lower than pH 3.0. A neutral buffer may adjust the pH of the skin to between about pH 6 to 8. A mildly alkaline buffer may adjust the pH of the skin to between about pH 8 to 10. The buffer contains an acid, neural or alkali buffering component and a pharmaceutically acceptable carrier, vehicle or excipient. The buffer is susceptible to neutralisation to the average normal pH of the surface of the skin over time by normal skin processes such as perspiration. Acid buffers may be an organic acid, inorganic acid or mixture thereof. Suitable acidic buffers include lactic acid, citric acid, sorbic acid, glycolic acid, malic acid, gluconic acid, glucoronic acid, succinic acid, sodium citrate, sodium sulfate, phosphoric acid, sodium bisulfate, potassium bisulfate and mixtures thereof.

It will be appreciated by one of skill in the art that appropriate dosages of the active compounds, and compositions comprising the active compounds, can vary from patient to patient.

A composition may be administered alone or in combination with other treatments, either simultaneously or sequentially dependent upon the condition to be treated.

Plant Aspartic Proteases

In this specification a "plant aspartic protease" refers to and includes aspartic proteases that can be obtained from plant cells, or tissue, including whole plants. Plant aspartic proteases include cardosins, cyprosins, cenprosins, phytepsins and cynarases. In some cases, the plant aspartic protease according to the invention is not a phytepsin. As used herein the term "plant aspartic protease" includes mutants of such proteases, particularly mutants in which the PSI domain has been made non-functional. It is preferred that the mutation does not inactivate the aspartic protease function of the protein. In preferred embodiments the mutation is such that the resulting polypeptide retains at least 50%, more preferably one of at least 60%, 65%, 70%, 75%, 80%, 85%, 86%, 87%, 88%, 89%, 90%, 91%, 92%, 93%, 94%, 95%, 96%, 97%, 98% or 99% sequence identity with the amino acid sequence of the wild type aspartic protease.

The term "modified plant aspartic protease" as used herein describes a plant aspartic protease which contains one or more modifications as compared with a wild type plant aspartic protease. For example, it may contain one or more amino acid deletions, substitutions or additions as compared to the sequence of the plant aspartic protease as produced in a plant.

Cardosins are examples of plant aspartic proteases, obtained from cardoon (Cynara cardunculus). The amino acid sequence of Cardosin A and Cardosin B is known (see SEQ ID NOs: 5 and 6).

The inventors have developed a heterologous method of production for plant aspartic proteases in a GRAS yeast (K. lactis) that could be effectively transferred to scale-up production. They have used the K. lactis Protein Expression System from New England Biolabs and several optimization procedures were undertaken in order to enhance protein expression and secretion levels. Cardosin A and Cardosin B (a vacuolar and an extracellular aspartic protease from cardoon (Cynara cardunculus), respectively) were used as working models.

Although some trafficking mechanisms in plants appear to be similar to those in yeasts there are several variations, particularly regarding the presence in plants of multiple vacuole types, that could result in the non-recognition of aspartic protease VSS's by yeast vacuolar sorting receptors. In fact, other plant VSS's of the CTPP type were previously shown not to be recognized in yeasts. Conversely, the results described herein indicate that some VSS's identified in plant aspartic proteases are recognized by yeast trafficking mechanisms and can be used to redirect protein sorting. These results show that the PSI domain is functional in plants and yeasts.

Plant Specific Insert (PSI)

When the inventors generated a construct of Cardosin B (which is normally localised extracellularly), lacking the PSI domain and expressed this in the K. lactis yeast, higher levels of expression and secretion were observed in the absence of the PSI, when compared to the full-length wild type construct. These results demonstrate that removal of the PSI domain from all plant aspartic proteases (either vacuolar or secreted) may have a positive impact on their secretion, in yeasts or in plants.

The PSI is an insertion of approximately 100 amino acids located between the N-terminal domain and a C-terminal domain of the precursor "preproenzymes" of the majority of plant aspartic proteases so far identified. The PSI is only identified in plant aspartic proteases, and is highly similar to saposins and saposin-like proteins, whose biological function has not been completely established. Structurally, the PSI comprises five amphipathic α-helices folded into a compact globular domain and linked with each other by three disulphide bridges (discussed in Simoes and Faro 2004[3]). The PSI sequence shown no homology with mammalian or microbial aspartic proteases but is highly similar to that of saposin-like proteins (SAPLIPs). A unique feature of the PSI is the swap of the N- and C-terminal portions of the saposin-like domain, where the C-terminal portion of one saposin is linked to the N-terminal portion of the other saposin. Hence the PSI is not a true saposin but a swaposin.

The plant aspartic proteases described herein may lack a functional PSI domain. The PSI domain may be entirely or partially deleted, or mutated such that it is rendered non functional. Mutation may involve modification of an oligonucleotide sequence encoding the aspartic protease. For example, the modification may be an addition, deletion, insertion or substitution in the coding sequence.

A PSI domain may have substantial identity to SEQ ID NO: 3, or SEQ ID NO: 4. A PSI domain may have at least 70% identity, at least 75% identity, at least 80% identity, at least 85% identity, at least 90% identity, at least 95% identity, at least 98% identity, or 100% identity to SEQ ID NO: 3 or SEQ ID NO: 4.

The PSI domain may have a length of any one of 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, or 150, amino acids. The PSI domain may have a length in the range 80, to 120 amino acids, or 90 to 110 amino acids, or 95 to 105 amino acids, or 98 to 108 amino acids. The PSI domain may have a minimum length of about 80 amino acids, more preferably one of 81, 82, 83, 84, 85, 86, 87, 88, 89, 90, 91, 92, 93, 94, 95, 96, 97, 98, 99, 100, 101, 102, 103, 104, 105, or 106 amino acids. The PSI domain may have a maximum length of about 130 amino acids, more preferably one of 100, 101, 102, 103, 104, 105, 106, 107, 108, 109, 110, 111, 112, 113, 114, 115, 116, 117, 118, 119, 120, 121, 122, 123, 124, 125, 126, 127, 128, or 129 amino acids.

The PSI domain of a plant aspartic protease functions to regulate trafficking of cardosins in the cell, for example targeting the protein to the vacuole. Thus, plant aspartic proteases according to the invention, which lack a functional PSI domain have altered trafficking, for example as compared to plant aspartic proteases that contain a complete PSI domain. For example, a modified aspartic protease that lacks a functional PSI domain may not be targeted to the vacuole, whereas the unmodified aspartic protease, such as the wild type protein, might be targeted to the vacuole.

The skilled person may readily determine whether an aspartic protease lacks a functional PSI domain by any suitable method known in the art. For example agents known to affect protein trafficking (e.g. glycosidases) may be applied to a cell to determine whether trafficking of the modified aspartic protease is affected by the agent in the same or a similar way to the complete, or wild type, plant aspartic protease. Alternatively, or additionally, subcellular fractionation may be used to determine whether the modified and complete, or wild-type, aspartic proteases are present in a similar distribution within a cell. Alternatively, or additionally, immunocytochemistry may be used to determine whether the protein is secreted from the cell, or present in a different cellular compartment, to a complete, or wild type, plant aspartic protease.

The lack of a functional PSI domain may be sufficient to stop the plant aspartic protease collecting in the vacuole and/or to increase secretion of the plant aspartic protease from the cell. In some cases, the lack of a functional PSI domain may entirely prevent the plant aspartic protease being localised to the vacuole such that substantially all of the plant aspartic protease produced by the cell is secreted from the cell.

The plant aspartic acid which lacks a functional PSI domain may be any plant aspartic acid. Preferably, the plant aspartic acid is from the Cardosin family of plant aspartic proteases, i.e. a mutant or modified Cardosin that lacks a functional PSI domain. In some cases the plant aspartic protease may be further mutated.

Modification of the PSI domain to render it non-functional may affect the kinetic properties of the plant aspartic protease. For example, the modified plant aspartic protease may be less caseinolytic as compared to the naturally occurring, or wild-type, plant aspartic protease. In some cases, modification of the PSI may increase the specificity of the plant aspartic protease for a substrate. For example, it may increase the specificity of the plant aspartic protease for α-casein.

Pro Segment

The prosegment is located in the N-terminal of plant aspartic proteases. It is present in the precursor protein and is normally removed by proteolysis during production of the mature, active, enzyme from the inactive zymogen. In some cases, the plant aspartic proteases according to the invention are expressed with a prosegment. The prosegment comprises approximately 40 amino acids.

C-Terminal Sequence

The C-terminal sequence is a putative enzyme sorting signal. Certain plant aspartic proteases may lack 1, 2, 3, 4, 5, 6, 7, 8, 9 or 10 amino acid residues, preferably 4 amino acids, from the C terminus, as compared to the naturally occurring form of the aspartic protease. For example, modified cardosin A according to the invention may lack AEAA from the C-terminus and cardosin B may lack AEAV.

Linkers

As used herein, the term "linker" denotes a series of amino acid resides which are introduced into a protein sequence to replace amino acid residues which have been removed. For example, the plant aspartic proteases of the present invention lack a functional PSI domain. Where the PSI domain is fully or partially deleted from the plant aspartic protease of the invention, the deleted amino acids may be replaced by a linker. The linker may allow two or more regions of the protein containing it to fold into the correct three dimensional configuration.

The linker may comprise one or more amino acids. The amino acids may all be the same, for example a plurality of glycine residues. Alternatively, the amino acids may be different. The linker may comprise a sequence corresponding to a scrambled sequence of the PSI domain.

The linker may comprise between 1 and 100, between 1 and 50, between 1 and 25 or between 1 and 10 amino acids. The linker may comprise 2, 3, 4, 5, 6, 7, 8, 9 or 10 amino acids. In some cases, the linker consists of 1 to 7 amino acid residues.

The presence of a linker may affect the kinetic properties of the plant aspartic protease. For example, the introduction of a linker may render the plant aspartic protease less caseinolytic as compared to the naturally occurring, or wild-type, plant aspartic protease. In some cases, the linker may increase the specificity of the plant aspartic protease for a substrate. For example, the introduction of a linker may increase the specificity of the plant aspartic protease for α-casein.

Cardosins

In this specification, a Cardosin nucleic acid may be any nucleic acid (DNA or RNA) having a nucleotide sequence which encodes a polypeptide having a specified degree of sequence identity to one of SEQ ID No.s 5 and 6 to an RNA transcript of any one of these sequences, to a fragment of any one of the preceding sequences or to the complementary sequence of any one of these sequences or fragments. Alternatively a Cardosin nucleic acid may be one that hybridises to one of these sequence under high or very high stringency conditions. The specified degree of sequence identity may be from at least 60% to 100% sequence identity. More preferably, the specified degree of sequence identity may be one of at least 65%, 70%, 75%, 80%, 85%, 86%, 87%, 88%, 89%, 90%, 91%, 92%, 93%, 94%, 95%, 96%, 97%, 98% or 99% identity.

In this specification, a Cardosin polypeptide may be any peptide, polypeptide or protein having an amino acid sequence having a specified degree of sequence identity to one of SEQ ID NO.s 1, 2, 5 or 6 or to a fragment of one of these sequences. The cardosin may be, or have a specified degree of sequence identity to, cardosin A as deposited at GenBank under accession number Q9XFX3.1 (GI: 75267434). The cardosin may be, or have a specified degree of sequence identity to, cardosin B as deposited at GenBank under accession number Q9XFX4.1 (GI: 75338567).

The specified degree of sequence identity may be from at least 60% to 100% sequence identity. More preferably, the specified degree of sequence identity may be one of at least 65%, 70%, 75%, 80%, 85%, 86%, 87%, 88%, 89%, 90%, 91%, 92%, 93%, 94%, 95%, 96%, 97%, 98% or 99% identity.

Sequence Identity

Percentage (%) sequence identity is defined as the percentage of amino acid residues in a candidate sequence that are identical with residues in the given listed sequence after aligning the sequences and introducing gaps if necessary, to achieve the maximum sequence identity, and not considering any conservative substitutions as part of the sequence identity. Sequence identity is preferably calculated over the entire length of the respective sequences.

Alignment for purposes of determining percent amino acid sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

In certain aspects the invention concerns compounds which are isolated peptides/polypeptides comprising an amino acid sequence having a sequence identity of at least 60% with a given sequence. Alternatively, this identity may be any of 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sequence Identity.

Identity of nucleic acid sequences may be determined in a similar manner involving aligning the sequences and introducing gaps if necessary, to achieve the maximum sequence identity, and calculating sequence identity over the entire length of the respective sequences.

In certain aspects the invention concerns compounds which are isolated nucleic acids comprising a nucleotide sequence having a sequence identity of at least 60% with a given sequence. Alternatively, this identity may be any of 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sequence identity.

Certain aspects of the invention relate to complete plant aspartic proteases (i.e. comprising substantially all domains present in the wild-type protein). For example, Cardosin A may have an amino acid sequence having a specified degree of sequence identity to SEQ ID NO: 3, or Cardosin B may have an amino acid sequence having a specified degree of sequence identity to SEQ ID NO: 4.

Preferably, the Cardosins of the invention lack a functional PSI domain. For example, Cardosin B may have an amino acid sequence having a specified degree of sequence identity to SEQ ID NO: 1, and Cardosin A may have an amino acid sequence having a specified degree of sequence identity to SEQ ID NO: 2.

In certain aspects of the invention, the compound of the invention may a be a protein fragment which retains the properties and/or therapeutic or cosmetic effects of the plant aspartic proteases described herein. For example, the compound may be a fragment of Cardosin A or B which has protease activity and/or induces skin desquamation.

A fragment may comprise a nucleotide or amino acid sequence encoding a portion of the corresponding full length sequence. In this specification the corresponding full length sequence may be one of SEQ ID No.s 1, 2, 5, or 6. Said portion may be of defined length and may have a defined minimum and/or maximum length.

Accordingly, the fragment may comprise at least, i.e. have a minimum length of, 10, 11, 12, 13, 14, 15, 16, 17, 18, 19, 20, 25, 30, 40, 50, 60, 70, 80, 85, 90, 95, 96, 97, 98 or 99% of the corresponding full length sequence. The fragment may have a maximum length, i.e. be no longer than, 10, 11, 12, 13, 14, 15, 16, 17, 18, 19, 20, 25, 30, 40, 50, 60, 70, 80, 85, 90, 95, 96, 97, 98 or 99% of the corresponding full length sequence. The fragment may have a length anywhere between the said minimum and maximum length.

The fragment may comprise at least, i.e. have a minimum length of, at least 100, 120, 140, 160, 180, 200, 220, 240, 260, 280, 300, 320, 340, 360, 377, 380, 383, 400, 420, 440, 460, 480 or 500 amino acids. The fragment may have a maximum length, i.e. be no longer than, 220, 240, 260, 280, 300, 320, 340, 360, 377, 380, 383, 400, 420, 440, 460, 480 or 483 amino acids.

Although wild type plant aspartic proteases will be useful in the therapeutic and cosmetic applications described herein, in some embodiments the plant aspartic protease may be a mutant or modified plant aspartic protease, such as a mutant or modified Cardosin. The plant aspartic protease may be mutated relative to the wild-type or genomic plant aspartic protease, carrying one or more alterations to the nucleic acid encoding the plant aspartic protease and/or to the amino acid sequence of the plant aspartic protease. The alteration may take the form of an addition, insertion, substitution or deletion.

In some embodiments of the invention the plant aspartic protease is mutated such that it does not have a functional PSI domain. In some cases, the PSI domain is entirely or substantially absent. In others at least one mutation is included in the protein and/or nucleic acid sequence such that the PSI domain of the aspartic protease is not fully transcribed, is incorrectly transcribed, or is otherwise non functional. Mutations may be point mutations or larger mutations, wherein one or more base pairs of the nucleic acid sequence encoding the aspartic protease are added, substituted, deleted or inserted. In some cases, the mutation is one that causes the subsequent nucleic acids to be transcribed out of frame, thereby producing a non-functional protein product. In other cases, mutation of a single base pair causes an alteration in the protein sequence such that the protein product is non functional. Where the mutation causes subsequent nucleic acids to be transcribed out of frame it may be necessary to include a further change downstream of the first mutation in order to restore transcription of a subsequent part of the protein, e.g. after some or all of the PSI domain, back into frame.

Methods for introducing mutations are known in the art, and the skilled person will readily appreciate suitable methods for creating a modified or mutant plant aspartic protease according to the invention. Preferably, mutations are introduced by site directed mutagenesis, for example through PCR mutagenesis. PCR mutagenesis is a method for generating point mutations on a double stranded plasmid and involves the use of two synthetic oligonucleotide primers containing the desired mutation, each complementary to the opposite strands of a vector containing the plant aspartic protease to be mutated.

Methods of Producing a Plant Aspartic Protease

Plant aspartic proteases may be produced according to any method known in the art, such as microbial fermentation, plant, insect or mammalian cell culture.

Certain methods according to the invention involve expressing a plant aspartic protease that lacks a functional PSI domain in a cell. The method optionally further comprises the step of collecting plant aspartic protease that has been secreted from the cell.

Molecular biology techniques suitable for the producing plant aspartic proteases according to the invention in cells are well known in the art, such as those set out in Sambrook et al., *Molecular Cloning: A Laboratory Manual*, New York: Cold Spring Harbor Press, 1989

The plant aspartic protease may be expressed from a nucleotide sequence encoding the plant aspartic protease. The nucleotide sequence may be contained in a vector present in the cell, or may be incorporated into the genome of the cell.

A "vector" as used herein is an oligonucleotide molecule (DNA or RNA) used as a vehicle to transfer foreign genetic material into a cell. The vector may be an expression vector for expression of the foreign genetic material in the cell. Such vectors may include a promoter sequence operably linked to the nucleotide sequence encoding the gene sequence to be expressed. A vector may also include a termination codon and expression enhancers. Any suitable vectors, promoters, enhancers and termination codons known in the art may be used to express plant aspartic proteases from a vector according to the invention. Suitable vectors include plasmids, binary vectors, viral vectors and artificial chromosomes. (e.g. yeast artificial chromosomes).

In this specification the term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. Where appropriate, the resulting transcript may then be translated into a desired protein or polypeptide.

Any cell suitable for the expression of polypeptides may be used for producing plant aspartic proteases according to the invention. The cell may be a prokaryote or eukaryote. Preferably the cell is a eukaryotic cell such as a yeast cell, a plant cell, insect cell or a mammalian cell. In some cases the cell is not a prokaryotic cell because some prokaryotic cells do not allow for the same post-translational modifications as eukaryotes. In addition, very high expression levels are possible in eukaryotes and proteins can be easier to purify from eukaryotes using appropriate tags. Specific plasmids may also be utilised which enhance secretion of the protein into the media.

In some embodiments the cell is not a plant cell, or a plant protoplast cell.

In some preferred embodiments the cell is a fungi (including yeasts and molds) or microbial eukaryote, or single coil eukaryote, preferably a yeast of the genus *Kluyveromyces, Rhizomucor, Endothia, Aspergillus* or *Saccharomyces*.

Suitable yeast cells include *Kluyveromyces lactis, Kluyveromyces marxianus, Rhizomucor meihei, Endothia parasitica, Rizomucor pusillus, Pichia pastoris, Aspergillus niger, Aspergillus oryzae* and *Saccharomyces cerevisae*. The yeast may be a GRAS (Generally Regarded As Safe) yeast, i.e. a yeast that has GRAS status from the Food and Drug Administration (FDA).

Methods of producing the plant aspartic protease may involve culture or fermentation of a eukaryotic cell modified to express the plant aspartic protease. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted aspartic protease. Culture, fermentation and separation techniques are well known to those of skill in the art.

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express a plant aspartic protease, the plant aspartic protease is preferably isolated. Any suitable method for separating proteins from cell culture known in the art may be used. In order to isolate a protein of interest from a culture, it may be necessary to first separate the cultured cells from media containing the protein of interest. If the protein of interest is secreted from the cells, the cells may be separated from the culture media that contains the secreted protein by centrifugation. If the protein of interest collects within the cell, for example in the vacuole of the cell, it will be necessary to disrupt the cells prior to centrifugation, for example using sonification, rapid freeze-thaw or osmotic lysis. Centrifugation will produce a pellet containing the cultured cells, or cell debris of the cultured cells, and a supernatant containing culture medium and the protein of interest.

It may than be desirable to isolate the protein of interest from the supernatant or culture medium, which may contain other protein and non-protein components. A common approach to separating protein components from a supernatant or culture medium is by precipitation. Proteins of different solubilities are precipitated at different concentrations of precipitating agent such as ammonium sulfate. For example, at low concentrations of precipitating agent, water soluble proteins are extracted. Thus, by adding different increasing concentrations of precipitating agent, proteins of different solubilities may be distinguished. Dialysis may be subsequently used to remove ammonium sulfate from the separated proteins.

Other methods for distinguishing different proteins are known in the art, for example ion exchange chromatography and size chromatography. These may be used as an alternative to precipitation, or may be performed subsequently to precipitation.

Once the protein of interest has been isolated from culture it may be necessary to concentrate the protein. A number of methods for concentrating a protein of interest are known in the art, such as ultrafiltration or lyophilisation.

A plant aspartic protease that has been isolated from a cell may be mixed with a carrier, adjuvant or diluent to form a product comprising a composition containing the plant aspartic protease. The product formed may be of any kind, e.g. liquid, solid, powder, cream and may be suitable for at least any of the following uses: as a cosmetic or therapeutic preparation, as a detergent or washing powder, as a food modifier, as a meat tenderiser, as a stain remover, as a leather softener, as a rennet substitute.

Methods for Promoting Accumulation of a Polypeptide of Interest

The invention also provides methods for promoting the accumulation of a polypeptide of interest in the vacuole of a cell, particularly a plant cell. Such methods involve expressing a polypeptide construct in the cell, the construct comprising the amino acid sequence of the polypeptide of interest and the amino acid sequence of a PSI domain. The amino acid sequences are preferably covalently linked to form a single contiguous amino acid sequence forming the polypeptide construct. As such, in some embodiments, the polypeptide construct may be a fusion protein.

The PSI domain may be included in the amino acid sequence of the construct at any position. In some embodiments the PSI domain may be added at any one of the N-terminus, C-terminus or a position between the N- and C-termini.

The polypeptide of interest can be any polypeptide, but is preferably not a polypeptide that normally (i.e. in the wild type sequence) encodes a PSI domain. For example, in some embodiments the polypeptide of interest is not an aspartic protease, and in some embodiments the polypeptide of interest is not a plant aspartic protease.

The polypeptide of interest is preferably a polypeptide that forms a protein having a measurable activity, e.g. binding to another molecule, or enzyme activity. The polypeptide construct preferably retains such a measurable activity, although the level of activity may be reduced or increased compared to the wild type polypeptide of interest. As such, the polypeptide will typically have a minimum length of at least about 50 amino acids, and more preferably one of about 60, 70, 80, 90, 100, 110, 120, 130, 140, 150, 160, 170, 180, 190, 200, 210, 220, 230, 240, 250, 260, 270, 280, 290, or 300 amino acids.

In some other embodiments the polypeptide of interest may be a small peptide, and may have a length of less than about 50 amino acids.

The polypeptide construct may be expressed from a nucleotide sequence encoding the polypeptide construct. The nucleotide sequence may be contained in a vector present in the cell, or may be incorporated into the genome of the cell.

Molecular biology techniques suitable km the producing plant aspartic protcascs according to the invention in cells are well known in the art, such as those set out in Sambrook et al., *Molecular Cloning: A Laboratory Manual*, New York: Cold Spring Harbor Press, 1989

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

EXAMPLES

Example 1—Synthesis of Cardosin B in *K. lactis*

Strains and Growth Conditions

All plasmid constructions and propagations were performed using the *Escherichia coli* strain Top10F' (Invitrogen). The bacterial cells were grown at 37° C. in LB (Miller's Formulation—Invitrogen) liquid and solid (1.5% agar) medium, supplemented with ampicillin at 100 µg/ml (GE-Healthcare). The *Kluyveromyces lactis* GG799 strain was purchased from New England Biolabs and used as host strain to the recombinant protein expression studies. *K. lactis* cells were grown and maintained in YPD media (2% bactopeptone, 1% yeast extract, 2% glucose) whereas the expression experiments were performed in YPGal (2% bactopeptone, 1% yeast extract, 4% galactose) as culture media, both at 30° C. with shaking. The recombinant *K. lactis* cells were selected on solid Yeast Carbon Base (New England Biolabs) supplemented with 5 mM acetamide (New England Biolabs) plates.

proCardosinBΔPSI pKLAC1 Sub Cloning

The cloning and subcloning procedures were performed according to the manufacturers' instructions and using standard molecular biology cloning techniques. The construct proCardosinB lacking the PSI region (pCBΔPSI, also referred to herein as Bwo) was amplified by PCR, using the construct pCBΔPSI/TA as template, in order to introduce upstream and downstream of the cDNA the restriction sites XhoI and SalI, respectively. The pair of oligonucleotides used in the PCR reaction were:

```
pCB-XhoI
(CTCGAGAAAAGAATGGTCTCCAACGGCGGATTGCTTC
[SEQ ID NO: 7])
and pCB-SalI
(GTCGACTCAAACTGCTTCTGCAAATCCCACTCGTAAC
[SEQ ID NO:8]).
```

After amplification the PCR product was cloned into pGEM (Promega) cloning vector and afterwards subcloned into the integrative expression pKLAC1 (NEB). The subcloning process was performed by cleavage/ligation at the XhoI/SalI restriction sites, resulting in pCBΔPSI cloning in frame with the α-mating factor secretion leader sequence.

*K. lactis* Recombinant Strains Construction

The recombinant plasmid pCBΔPSI/pKLAC1 was linearized by SacII (NEB) digestion, in order to obtain the insertion cassette fragments that were afterwards used in *K. lactis* transformation step. A total of 2 µg DNA was used in *K. lactis* GG799 transformation. This process was performed by electroporation with a "Gene Pulser" (BioRad) apparatus, using the following electroporation conditions: 1.5 KV, 25 mF and 200 Ohm. The positive transformants were selected based on their ability to growth on YCB acetamide media, and the multi-integrants clones selected by whole-cell PCR, following the instructions described on the "*K. lactis* expression Kit" protocols (NEB).

Heterologous pCBΔPSI Mutants Expression and Purification

An integrative recombinant *K. lactis* clone was selected for pCBΔPSI construct and was grown in YPD media, at 30° C. with shaking, for 16 h. The cultures were diluted to an OD600 nm of 0.3 in YPGal media and incubated at 30° C., with shaking for and 4 days. Thereafter the cultures were centrifuged and the supernatants sequentially filtered through 0.8 µm, 0.45 µm and 0.2 µm filters. The samples were concentrated and activated by dilution 1:10 with 0.5M sodium acetate buffer pH4.0, at 37° C. A size exclusion chromatography was the first purification step. The samples were applied to a S200 26/60 column (GE-Healthcare) and the proteins were eluted with buffer 20 mM Tris-HCl pH7.5, 0.1M NaCl at a flow rate of 1 ml/min. Fractions were pooled and applied to an ionic exchange on a Mono Q, using the buffer 20 mM Tris-HCl pH7.5. The proteins were then eluted with a linear gradient of 0-0.5M NaCl, at a flow rate of 0.75 ml/min. Both expression and purification procedures were followed by SDS-PAGE analysis (see FIG. 1).

This expression and purification method results in the production of a plant origin-based enzyme in considerable amounts (3 mg/L) and with a high purity level.

Example 2—pAP Induces Desquamation

3D Skin Model ("EpiSkin"-SkinEthic (L'Oreal®), and "Epidermal Skin Test" (EST-1000-CellSystems))

Two rounds of experiments were performed using skin models. In both experiments the enzyme sample (hereby named pAP) was applied to model surface and each model was incubated for different incubation times at 37° C., in an atmosphere of 5% $CO_2$. After incubation, each sample was collected from the top of the model, centrifuged and the detached cells were counted on a hemocytometer. The models surface was washed with PBS, and the models were transferred to a new plate with fresh culture medium and incubated at the same conditions.

Figure 2:
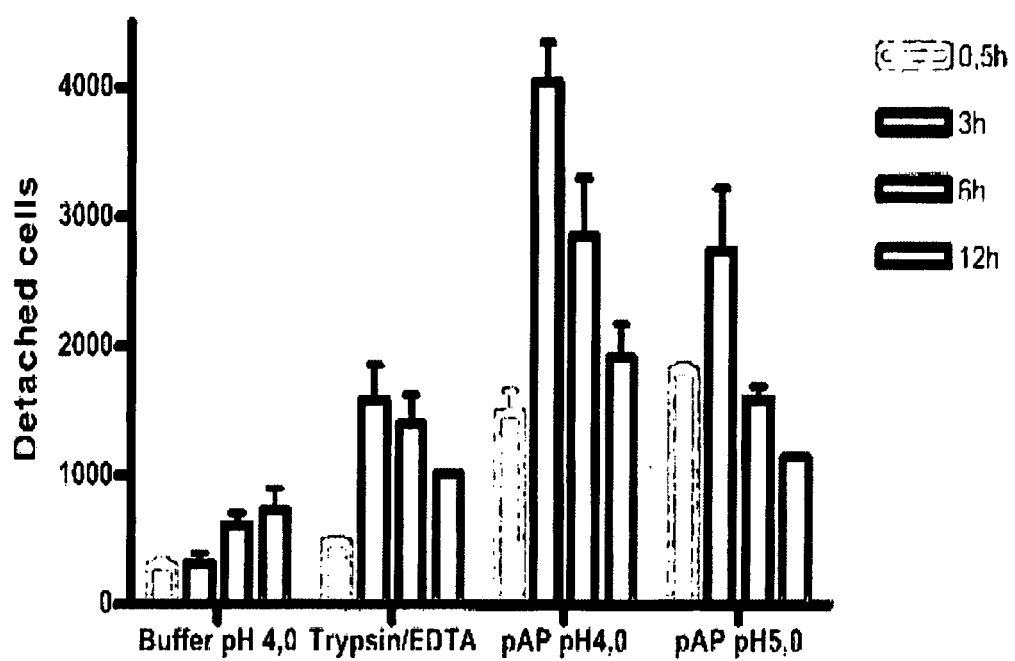
FIG. 2. Effect of pAP enzymatic activity on epidermal cell desquamation. The aspartic protease was applied to model surface at a final concentration of 1 mg/ml for 30 min, 3 h, 6 h and 12 h. The detached cells were counted on a hemocytometer.

In the first round of experiments the desquamation activity was tested for three incubation times and two different pH values. The pAP was tested in a final formulation of 0.1% (w/v), in 0.1M buffer sodium citrate pH 4.0 and pH 5.0. The sample Trypsin/EDTA (0.025%) was used as positive control and a sample of buffer pH 4.0 as negative control. The results are shown in FIG. 2.

Figure 3:
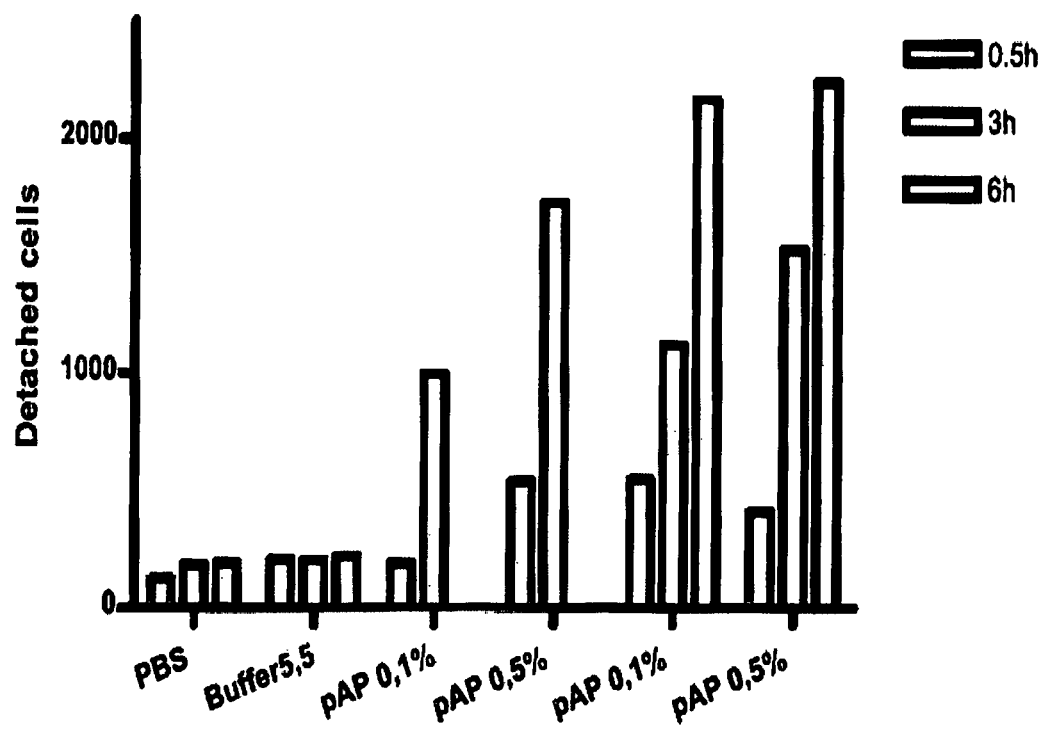
FIG. 3. Study of enzymatic desquamation of skin models. The skin models were exposed to the pAP at the final concentrations 0.1% and 0.5%, at pH 4.5 and pH 5.5 for the incubations times: 30 min, 3 h and 6 h. The detached cells were counted by using a Neubaur chamber.
Figure 4:
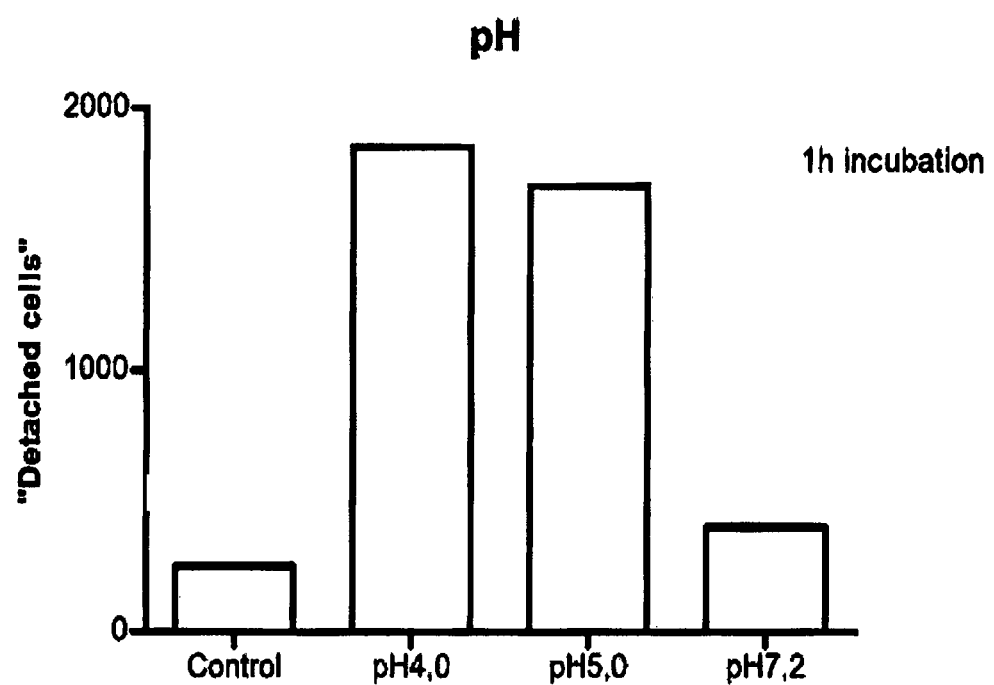
FIG. 4. Effect of pH on the enzymatic desquamation activity of pAP. The pAP was tested at a final concentration of 0.1%, at different pHs. After 1 h incubation time the samples were collected from the models surface and the detached cells were counted.

In the second round of experiments, the protein was tested for the concentrations 1 mg/ml (0.1%) and 5 mg/ml (0.5%) and for different incubation times. The pH dependence of desquamation activity was also studied. The model cell viability was determined by the MTT assay method, 42 h after the enzymatic incubation. The results are shown in FIGS. 3 and 4.

MTT Assay

Figure 5:
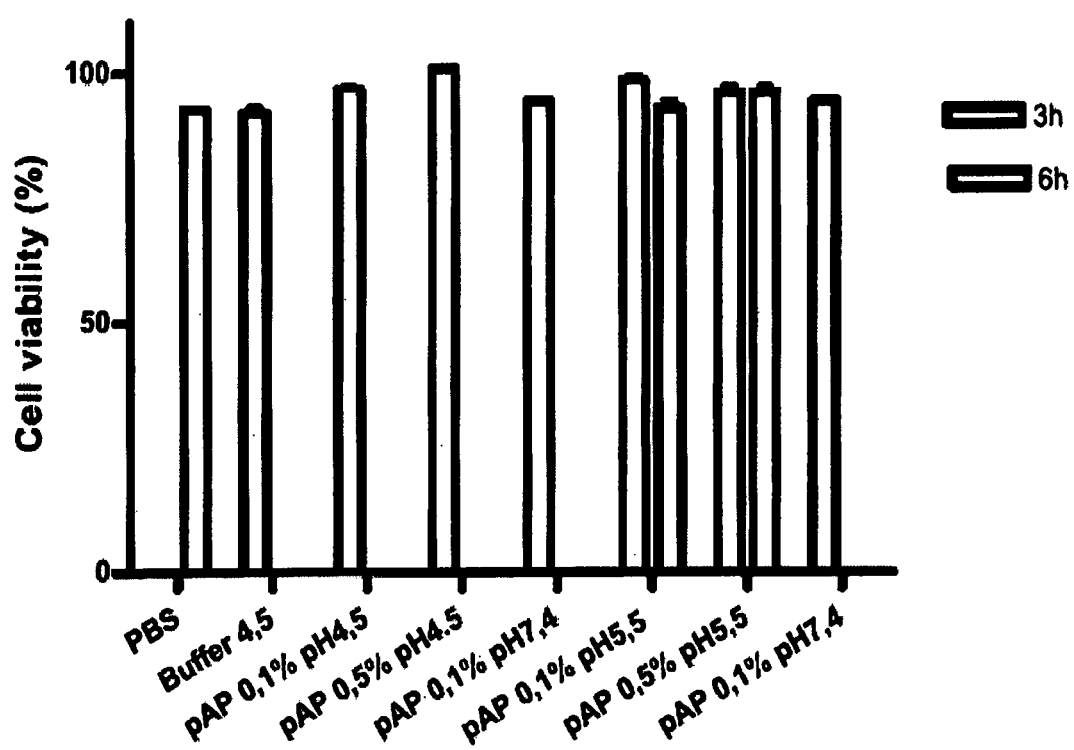
FIG. 5. Cell viability determination. The skin models exposed to pAP enzymatic activity were subjected to MTT assay in order determine the tissue cellular viability. After the detachment experiments, the models were incubated for 42 h at 37° C. atmosphere with 5% $CO_2$. The models were incubated in MTT assay reagent for 3 h, the formed dye was solubilized in isopropanol, and the absorbance was measured at 570 nm. For cell viability calculation, the absorbance of the model incubated with PBS was taken as 100%.

The MTT test was performed in order to test the enzyme effect on skin model cellular viability. After the exposure to enzymatic action, each model was incubated in fresh culture medium at 37° C. atmosphere with 5% $CO_2$, for 24 h. The medium was changed and the models were incubated for another 18 h time period at the same conditions. After this recovery time, the models were incubated with the MTT solution for 3 h and the converted dye was solubilized by using isopropanol. The absorbance was measured at 570 nm. See FIG. 5.

The pAP enzyme was shown to have an epidermal cell desquamation activity. The results indicate that pAP is approximately 13 times more effective at causing cellular shedding than a control of buffer solution and approximately 3 times more effective at causing cellular shedding than the positive control Trypsin/EDTA (0.025% w/v), at a pH of 4 and at a concentration of 0.1% (w/v), in 0.1 M buffer sodium citrate.

The MTT viability assay demonstrates that across a range of pH's and concentrations, the enzyme is well tolerated and could therefore be utilised at a range of concentrations for different therapeutic indications and non-therapeutic applications without damaging the remaining un-desquamated cells.

The pAP enzyme has greater desquamation capacity than either Renin or Cathepsin D (a mammalian aspartic protease involved in the natural skin desquamation process).

Example 3—Comparison of pAP with Two Different Aspartic Proteases

This set of experiments had as major goal the comparison between the enzymatic desquamation activity of two different aspartic proteases (Cathepsin D and Renin) and Cardosin B (pAP) activity. Additionally, the desquamation enzymatic activity pH dependence experiments were performed, for a shorter incubation time, in order to determine the effect of the normal skin neutralization process
Cardosin B, Cathepsin D and Renin Enzymatic Desquamation Activity ("EpiSkin"-SkinEthic (L'Oreal®))

Figure 6:
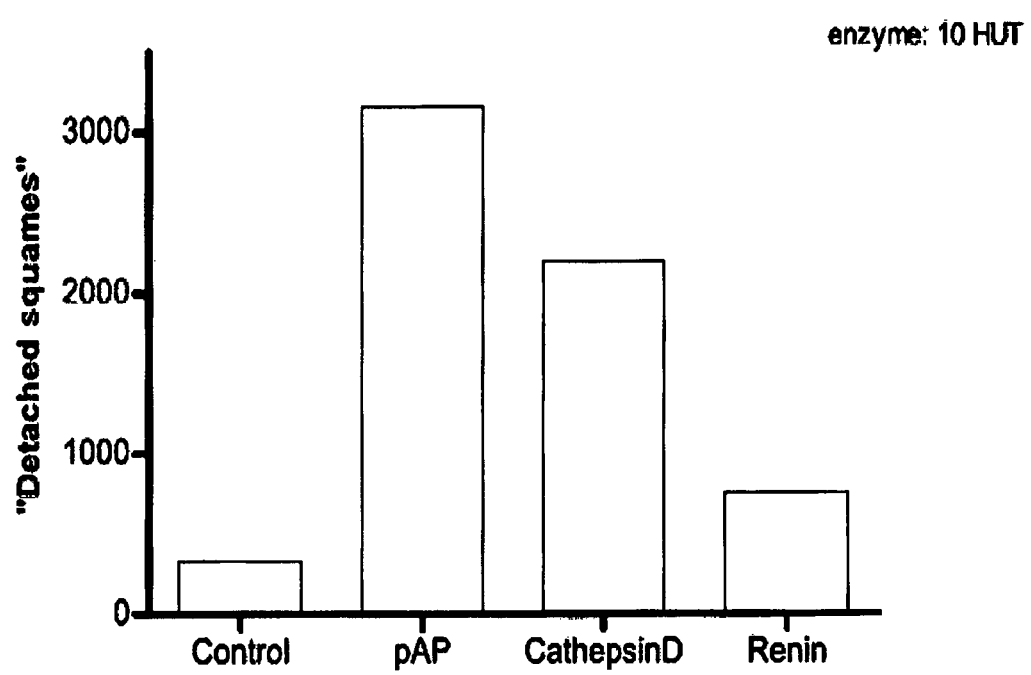
FIG. 6. Effect of different aspartic proteases on epidermal cell desquamation. The aspartic proteases were applied to model surface and after 4 h incubation time the detached cells were counted on a hemocytometer. About 10 HUT of each enzyme were tested in citrate buffer pH5.0 excepting for Renin that was tested at pH6.0.

One round of experiments was performed for each proteolytic enzyme, using Episkin models. As described above, the enzyme samples were applied to model surface and the models were incubated for 4 h, at 37° C., in an atmosphere of 5% $CO_2$. After incubation, each sample was collected from the top of the model, centrifuged and the detached squames were counted on a hemocytometer. The enzymes (130 HUT/mg) were tested using about 10 HUT enzyme units, in 0.1M citrate buffer pH 5.0. Renin was tested at its optimal pH-pH 6.0, and the citrate buffer pH 5.0 was used as negative control. See FIG. 6.

Enzymo Dosquamation Activity pH Dependence

The pH dependence of desquamation activity was studied, testing a shorter incubation period. After an injury, the skin recovery time is about 30 minutes to 1 h, if the agent is a non-toxic agent. In these assays, the pAP was incubated for 1 h, in citrate buffer pH 4.0, pH5.0, and in PBS pH7.0, at 37° C. in an atmosphere of 5% $CO_2$. See FIG. 7. Although displaying desquamation activity at pH 7, pAP activity is greatly enhanced at pH 4.0 and pH 5.0 what is consistent with the optimum pH of cardosins (ref 10)

REFERENCES

1 Vitale A & Hinz G, 2005. Trends in Plant Sci, 10(7): 316-323
2 Törmäkangas K et al, 2001. Plant Cell, 13: 2021-2032
3 Simões I & Faro C, 2004. Eur. J. Biochem. 271, 2067-2075
4 Törmäkangas K et al, 2001. Plant Cell, 13: 2021-2032
5 Ramalho-Santos M et al, 1998. Eur J Biochem, 255: 133-138
6 Duarte A S, et al, 2005. Current Drug Disc Tech, 2: 37-44
7 PCT Patent publication No WO9507687
8 Patent publication No JP2000247907
9 US patent publication No US2003040047
10 Verissimo P et al (1996) Eur J Biochem, 235(3):762-8.
11 Verissimo P et al (1996) Eur J Biochem, 762-768
12 Chu T C, 1997. Medicine, 25:30-33
13 Smithard A et al, 2001. Br J Dermatol, 145:274-279
14 Pearl A et al, 1998. N Z Med J, 111:269-271
15 Cunliffe W J, 1998. J Cutan Med Surg, 2(suppl 3):7-13
16 Fowler J F et al, 2008. J. Am Acad Dermatol, 59(5):772-80
17 Horn E J at al, 2007. J Am Acad Dermatol, 57(6):963-71
18 Egas C et al, 2000. J. Biol. Chem, 275, 38190-38196
19 Claverie-Martin et al, 2007. Industrial Enzymes 207-219

The invention claimed is:

1. An ointment, cream or emulsion composition comprising an isolated plant aspartic protease, wherein the isolated plant aspartic protease is a Cardosin, and wherein the isolated plant aspartic protease has at least 70% sequence identity to the full length of SEQ ID NO: 1 or SEQ ID NO: 2.

2. The ointment, cream or emulsion composition according to claim 1 wherein the plant specific insert (PSI) domain of the plant aspartic protease is entirely or partially deleted.

3. The ointment, cream or emulsion composition according to claim 1 wherein the composition additionally comprises a pharmaceutically or cosmetically acceptable carrier, adjuvant or diluent.

4. A method of medical treatment comprising administering a plant aspartic protease to the skin of a subject to induce skin desquamation in the subject, wherein the plant aspartic protease is a Cardosin, and wherein the plant aspartic protease has at least 70% sequence identity to the full length of SEQ ID NO: 1 or SEQ ID NO: 2.

5. The method of medical treatment according to claim 4 wherein the subject is suffering from a skin disorder or disease.

6. The method of medical treatment according to claim 4 wherein the subject is suffering from at least one of xerosis, eczema, acne, psoriasis or ichthyosis, and the method involves the treatment of at least one of xerosis, eczema, acne, psoriasis or ichthyosis.

7. The method of medical treatment according to claim 4 wherein the plant aspartic protease is Cardosin B or Cardosin A.

8. The method of medical treatment according to claim 4 wherein the plant specific insert (PSI) domain of the plant aspartic protease is entirely or partially deleted.

9. A cosmetic method for improving the appearance of the skin comprising administering a plant aspartic protease to the skin of a human, wherein the plant aspartic protease is a Cardosin, and wherein the plant aspartic protease has at least 70% sequence identity to the full length of SEQ ID NO: 1 or SEQ ID NO: 2, and wherein the plant aspartic protease induces skin desquamation in the human.

10. The cosmetic method according to claim 9, wherein the plant aspartic protease is Cardosin B or Cardosin A.

11. The cosmetic method according to claim 9, wherein the plant specific insert (PSI) domain of the plant aspartic protease is entirely or partially deleted.

* * * * *